US008871723B2

(12) United States Patent
Rubinstein et al.

(10) Patent No.: US 8,871,723 B2
(45) Date of Patent: Oct. 28, 2014

(54) GLYCAN MODIFIED SOLUBLE RECEPTORS AND BINDING PROTEIN AND THEIR USE

(75) Inventors: Menachem Rubinstein, Rehovot (IL); Ariel Werman, Jerusalem (IL); Ben Alkahe, Tel Aviv (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 784 days.

(21) Appl. No.: 12/598,511

(22) PCT Filed: Apr. 30, 2008

(86) PCT No.: PCT/IL2008/000574
§ 371 (c)(1),
(2), (4) Date: Nov. 2, 2009

(87) PCT Pub. No.: WO2008/135972
PCT Pub. Date: Nov. 13, 2008

(65) Prior Publication Data
US 2010/0087363 A1 Apr. 8, 2010

(30) Foreign Application Priority Data
May 3, 2007 (IL) .......................................... 182956

(51) Int. Cl.
*A61K 38/16* (2006.01)
*C07K 14/00* (2006.01)
*C07K 14/705* (2006.01)
*C07K 14/71* (2006.01)

(52) U.S. Cl.
CPC ........... *C07K 14/70578* (2013.01); *C07K 14/71* (2013.01); *C07K 14/705* (2013.01)
USPC ........................................ 514/21.2; 530/359

(58) Field of Classification Search
None
See application file for complete search history.

(56) References Cited

U.S. PATENT DOCUMENTS

| | | | |
|---|---|---|---|
| 5,958,408 A | 9/1999 | Griffiths et al. | |
| 5,965,131 A | 10/1999 | Griffiths et al. | |
| 6,858,578 B2 | 2/2005 | Heartlein et al. | |
| 2004/0115186 A1 | 6/2004 | Segal et al. | |
| 2004/0136986 A1* | 7/2004 | Raju ........................ | 424/144.1 |
| 2006/0040353 A1* | 2/2006 | Davidson et al. ........... | 435/69.1 |
| 2006/0275294 A1 | 12/2006 | Omoigui | |

FOREIGN PATENT DOCUMENTS

| | | |
|---|---|---|
| EP | 0 586 094 | 3/1994 |
| JP | 2002511264 | 4/2002 |
| WO | WO 92/01469 | 2/1992 |
| WO | WO-95/09652 | 4/1995 |
| WO | WO 2005/000227 | 1/2005 |
| WO | WO-2005/100584 | 10/2005 |
| WO | WO 2007/056812 | 5/2007 |

OTHER PUBLICATIONS

Bernini, F., S. R. Tanenbaum, et al. (1986). "Enhanced catabolism of low density lipoproteins in rat by lactosaminated Fab fragment. A new carrier of macromolecules to the liver." J Biol Chem 261 (20): 9294-9.
Bilheimer, D. W., N. J. Stone, et al. (1979). "Metabolic studies in familial hypercholesterolemia. Evidence for a gene-dosage effect in vivo." J Clin Invest 64(2): 524-33.
Brown, M. S. and J. L. Goldstein (1986). "A receptor-mediated pathway for cholesterol homeostasis." Science 232(4746): 34-47.
Cardona, F., F. J. Tinahones, et al. (2003). "The elevated prevalence of apolipoprotein E2 in patients with gout is associated with reduced renal excretion of urates." Rheumatology (Oxford) 42(3): 468-72.
Carey MC, Duane WC. Enterohepatic circulation. In: Arias IM, Boyer JL, Faustoet N, et al., eds. The Liver: Biology and Pathobiology. New York: Raven Press, 1994:719-767.
Civeira, F. (2004). "Guidelines for the diagnosis and management of heterozygous familial hypercholesterolemia." Atherosclerosis 173(1): 55-68.
Cummings, R. D., S. Kornfeld, et al. (1983). "Biosynthesis of N- and O-linked oligosaccharides of the low density lipoprotein receptor." J Biol Chem 258(24): 15261-73.
Do, K. Y., S. I. Do, et al. (1997). "Differential expression of LacdiNAc sequences (GalNAc beta 1-4GlcNAc-R) in glycoproteins synthesized by Chinese hamster ovary and human 293 cells." Glycobiology 7(2): 183-94.
Fischer, D. G., N. Tal, et al. (1993). "An antiviral soluble form of the LDL receptor induced by interferon." Science 262(5131): 250-3.
Fisher, C., D. Abdul-Aziz, et al. (2004). "A two-module region of the low-density lipoprotein receptor sufficient for formation of complexes with apolipoprotein E ligands." Biochemistry 43(4): 1037-44.
Gent, J. and I. Braakman (2004). "Low-density lipoprotein receptor structure and folding." Cell Mol Life Sci 61(19-20): 2461-70.
Goldsmith, D. R. and A. J. Wagstaff (2005). "Spotlight on etanercept in plaque psoriasis and psoriatic arthritis." BioDrugs 19(6): 401-3.
Grundy, S. M. (1983). "Absorption and metabolism of dietary cholesterol." Annu Rev Nutr 3: 71-96.
Hatters, D. M., C. A. Peters-Libeu, et al. (2006). "Apolipoprotein E structure: insights into function." Trends Biochem Sci 31(8): 445-54.
Heaney, M. L. and D. W. Golde (1998). "Soluble receptors in human disease." J Leukoc Biol 64(2): 135-46.
Horiuchi, S., Y. Sakamoto, et al. (2003). "Scavenger receptors for oxidized and glycated proteins." Amino Acids 25(3-4): 283-92.
Huang, X., C. Gottstein, et al. (1998). "Expression of soluble VEGF receptor 2 and characterization of its binding by surface plasmon resonance." Biochem Biophys Res Commun 252(3): 643-8.

(Continued)

*Primary Examiner* — Robert A Wax
*Assistant Examiner* — Jessica Worsham
(74) *Attorney, Agent, or Firm* — Marshall, Gerstein & Borun LLP

(57) ABSTRACT

An invention relates to a glycan-modified soluble receptor or binding protein of a cytokine, growth factor, lipoprotein or oxidized lipoprotein, modified to carry a terminal Gal, GlcNAc or GalNAc.

12 Claims, 2 Drawing Sheets

(56) References Cited

OTHER PUBLICATIONS

Hussain, M. M., D. K. Strickland, et al. (1999). "The mammalian low-density lipoprotein receptor family." Annu Rev Nutr 19: 141-72.
Idriss, H. T. and J. H. Naismith (2000). "TNF alpha and the TNF receptor superfamily: structure-function relationship(s)." Microsc Res Tech 50(3): 184-95.
Ishigaki, T., I. Ohki, et al. (2005). "Purification, crystallization and preliminary X-ray analysis of the ligand-binding domain of human lectin-like oxidized low-density lipoprotein receptor 1 (LOX-1)." Acta Crystallograph Sect F Struct Biol Cryst Commun 61(Pt 5): 524-7.
Johs, A., M. Hammel, et al. (2006). "Modular structure of solubilized human apolipoprotein B-100. Low resolution model revealed by small angle neutron scattering." J Biol Chem 281 (28): 19732-9.
Kataoka, H., N. Kume, et al. (2000). "Biosynthesis and post-translational processing of lectin-like oxidized low density lipoprotein receptor-1 (LOX-1). N-linked glycosylation affects cell-surface expression and ligand binding." J Biol Chem 275(9): 6573-9.
Kawar, Z. S., S. M. Haslam, et al. (2005). "Novel poly-GalNAcbetal-4GlcNAc (LacdiNAc) and fucosylated poly-LacdiNAc N-glycans from mammalian cells expressing beta1,4-N-acetylgalactosaminyltransferase and alpha ,3-fucosyltransferase." J Biol Chem 280(13): 12810-9.
Kita, T., N. Kume, et al. (2001). "Role of oxidized LDL in atherosclerosis." Ann N Y Acad Sci 947: 199-205; discussion 205-6.
Kong, W.-J., J. Liu, et al. (2006). "Human low-density lipoprotein receptor gene and its regulation." J. Molec. Med. 84(1): 29-36.
Mahley, R. W. (1988). "Apolipoprotein E: cholesterol transport protein with expanding role in cell biology." Science 240(4852): 622-30.
McCormack, P. L. and K. Wellington (2004). "Etanercept: in ankylosing spondylitis." BioDrugs 18(3): 199-205; discussion 206.
Murase, T., N. Kume, et al. (2000). "Identification of soluble forms of lectin-like oxidized LDL receptor-1." Arterioscler Thromb Vasc Biol 20(3).: 715-20.
Murray, C. J. and A. D. Lopez (1997). "Global mortality, disability, and the contribution of risk factors: Global Burden of Disease Study." Lancet 349(9063): 1436-42.
Nakajima, K., T. Nakano, et al. (2006). "The oxidative modification hypothesis of atherosclerosis: the comparison of atherogenic effects on oxidized LDL and remnant lipoproteins in plasma." Clin Chim Acta 367(1-2): 36-47.
Olofsson, S. 0. and J. Boren (2005). "Apolipoprotein B: a clinically important apolipoprotein which assembles atherogenic lipoproteins and promotes the development of atherosclerosis." J Intern Med 258(5): 395-410.
Parise et al., "Construction and in vitro functional evaluation of a low-density lipoprotein receptor/transferrin fusion protein as a therapeutic tool for familial hypercholesterolemia", Human Gene Therapy, 10(7):1219-1228 (1999).
Park, E. I., Y. Mi, et al. (2005). "The asialoglycoprotein receptor clears glycoconjugates terminating with sialic acid alpha 2,6GalNAc." Proc Natl Acad Sci U S A 102(47): 17125-9.
Rensen, P. C., L. A. Sliedregt, et al. (2006). "Stimulation of liver-directed cholesterol flux in mice by novel N-acetylgalactosamine-terminated glycolipids with high affinity for the asialoglycoprotein receptor." Arterioscler Thromb Vasc Biol 26(1): 169-75.
Rensen, P. C., S. H. van Leeuwen, et al. (2004). "Design and synthesis of novel N-acetylgalactosamine-terminated glycolipids for targeting of lipoproteins to the hepatic asialoglycoprotein receptor." J Med Chem 47(23): 5798-808.
Rice, K. G., V. H. Thomas, et al. (2003). "Probing the binding specificity of C-type lectins in vivo." Methods Enzymol 363: 90-104.
Robbesyn, F., R. Salvayre, et al. (2004). "Dual role of oxidized LDL on the NF-kappaB signaling pathway." Free Radic Res 38(6): 541-51.
Sawamura, T., N. Kume, et al. (1997). "An endothelial receptor for oxidized low-density lipoprotein." Nature 386(6620): 73-7.
Schwartzman, S., R. Fleischmann, et al. (2004). "Do anti-TNF agents have equal efficacy in patients with rheumatoid arthritis?" Arthritis Res Ther 6 Suppl 2: S3-S 11.
Segrest, J. P., M. K. Jones, et al. (2001). "Structure of apolipoprotein B-100 in low density lipoproteins." J Lipid Res 42(9): 1346-67.
Selmaj, K. W. (2000). "Tumour necrosis factor and anti-tumour necrosis factor approach to inflammatory demyelinating diseases of the central nervous system." Ann Rheum Dis 59 Suppl 1: i94-i102.
Shi, X., S. Niimi, et al. (2001). "Characterization of residues and sequences of the carbohydrate recognition domain required for cell surface localization and ligand binding of human lectin-like oxidized LDL receptor." J Cell Sci 114(Pt 7): 1273-82.
Simmons, T., Y. M. Newhouse, et al. (1997). "Human low density lipoprotein receptor fragment. Successful refolding of a functionally active ligand-binding domain produced in *Escherichia coli*." J Biol Chem 272(41): 25531-6.
Smirnova, I. V., T. Sawamura, et al. (2004). "Upregulation of lectin-like oxidized low-density lipoprotein receptor-1 (LOX-1) in endothelial cells by nitric oxide deficiency." Am J Physiol Renal Physiol 287(1): F25-32.
Spady, D. K. (1992). "Hepatic clearance of plasma low density lipoproteins." Semin Liver Dis 12(4): 373-85.
Tulenko, T. N. and A. E. Sumner (2002). "The physiology of lipoproteins." J Nucl Cardiol 9(6): 638-49.
Twisk, J., D. L. Gillian-Daniel, et al. (2000). "The role of the LDL receptor in apolipoprotein B secretion." J Clin Invest 105(4): 521-32.
Weigel et al., "Glycans as endocytosis signals: the cases of the asialoglycoprotein and hyaluronan/chondroitin sulfate receptors", Biochimica et Biophysica Acta—General Subjects, Elsevier Science Publishers, NL, 1572(2-3):341-363 (2002).
Westerlind, U., J. Westman, et al. (2004). "Ligands of the asialoglycoprotein receptor for targeted gene delivery, part 1: Synthesis of and binding studies with biotinylated cluster glycosides containing N-acetylgalactosamine." Glycoconj J 21(5): 227-41.
Xie, Q., S. Matsunaga, et al. (2004). "Human lectin-like oxidized low-density lipoprotein receptor-1 functions as a dimer in living cells." DNA Cell Biol 23(2): 111-7.
Yamamoto et al. "The Human LDL Receptor: A Cysteine-Rich Protein with Multiple Alu Sequnces in its mRNA", Cell 39: 27-38, 1984.
Zhang, H., X. J. Li, et al. (2003). "Identification and quantification of N-linked glycoproteins using hydrazide chemistry, stable isotope labeling and mass spectrometry." Nat Biotechnol 21(6): 660-6.
Zhou Honghui, "Clinical pharmacokinetics of etanercept: A fully humanized soluble recombinant tumor necrosis factor receitpr fusion protein", Journal of Clinical Pharmacology, 45(5):490-497 (2005).
International Search Report for PCT/IL2008/000574 dated Dec. 15, 2008.

\* cited by examiner

GLYCAN MODIFIED SOLUBLE RECEPTORS AND BINDING PROTEIN AND THEIR USE

FIELD OF THE INVENTION

The present invention relates to agents capable of clearance of undesired components from the circulation and to clinical use of said agents. Examples of such undesired components are proinflammatory cytokines, LDL, VLDL, oxidized LDL, remnant lipoproteins and growth factors.

BACKGROUND OF THE INVENTION

Soluble receptors and binding proteins are circulating proteins that bind with high affinity and specificity to various cytokines, growth factors, polypeptide hormones and other circulating effector proteins. In most cases, the soluble receptor corresponds to the extracellular, ligand-binding domain of the corresponding cell surface receptor. Such soluble receptors are generated either through mRNA splice variants that code for the soluble receptor or by shedding of the ligand-binding extracellular domain of the cell surface receptor. There are however some cytokine-binding proteins such as IL-18 binding protein (IL-18BP) and osteoprotegerin, which do not correspond to a cell surface receptor.

The existence of soluble receptors and the complex regulation of their production and function suggests that they have an important role in normal physiology and in response to disease, although in some cases they appear to contribute to the pathological process. For example, an important component of the allergic response is mediated by eosinophils whose production and activity are significantly stimulated by IL-5. In patients with allergic asthma, the level of mRNA encoding the membrane-bound IL-5 receptor in endo-bronchial biopsy samples increases with the severity of bronchial constriction. As treated patients recover from an acute asthmatic episode, expression of soluble IL-5 receptor mRNA increases, suggesting that the soluble IL-5 receptor may counteract the effects of IL-5 in the lung and its increased expression may effect recovery from asthma (Heaney and Golde 1998).

Due to their fundamental involvement in the pathogenesis of many diseases, cytokines constitute key targets for biotherapeutic approaches. The discovery that soluble forms of cytokine receptors are involved in the endogenous regulation of cytokine activity has prompted substantial interest in their potential application as immunotherapeutic agents. As such, soluble cytokine receptors have many advantages, including specificity, low immunogenicity and high affinity. The ability of many soluble cytokine receptors to inhibit the binding and biological activity of their ligands makes them very specific cytokine antagonists. Several pharmaceutical companies have generated a number of therapeutic agents based on soluble cytokine receptors and many of them are undergoing clinical trials. The most advanced in terms of clinical development is etanercept (Enbrel™, Amgen), a fusion protein between soluble TNF receptor Type II and the Fc region of human IgG1. This TNF-α antagonist was the first soluble cytokine receptor to receive approval for use in humans. In general, most agents based on soluble cytokine receptors have been safe, well-tolerated and have shown only minor side effects in the majority of patients. Soluble cytokine receptors constitute a new generation of therapeutic agents with tremendous potential for applications in a wide variety of human diseases (Idriss and Naismith 2000).

TNFα binds to two cognate receptors of molecular weight 55 and 75 kDa. Human TNFR-1 consists of 434 amino acids whilst TNFR-2 comprises 439 residues. These receptors share very limited homology in the extracellular region. The TNF receptor superfamily is defined by the presence of repeating units of cysteine clusters. TNF receptors are present on almost all known cell types with few exceptions, such as erythrocytes and unstimulated T lymphocytes. Receptor density ranges from 200-10,000 per cell. There seems to be no correlation between the number of receptors present on a cell and the magnitude or direction of the TNF-induced response. Soluble forms of TNFR-1 and TNFR-2 have been identified in human urine and in the serum of cancer patients. These probably regulate TNF's activity by decoying the ligand, thereby down-regulating the generated signals.

Many membrane bound receptors (including TNFR-1 and 2) have been identified thus far, forming what is known as the TNF receptor superfamily. Their molecular weight is in the range of 50-120 kDa. Members of the TNF receptor family belong to the type I transmembrane glycoproteins. A number of related receptors termed "decoy receptors" have also been identified, which function to sequester secreted ligands. Decoy receptors (DcR1, DcR2, and DcR3) sequester Trail (DcR1 and DCR2) and Fas (DcR3) ligands, thereby preventing apoptosis. In addition, a soluble non-membrane bound decoy receptor termed osteoprotegerin (OPG) has also been identified. Not many posttranslational modifications have been reported for the TNFR-1 family. TNFR-1 and TNFR-2 are both N-glycosylated, but only TNFR-2 is O-glycosylated. All other membrane receptors are also glycosylated (Idriss and Naismith 2000).

Rheumatoid arthritis (RA), a systemic disease, is the most common form of inflammatory arthritis. The disorder has a worldwide prevalence of about 1% and an annual incidence of 3 per 10,000 adults. RA is accompanied by significant morbidity and mortality. Depending on the severity of the disease at onset, the risk of disability can be as high as 33%, and mortality can be increased by as much as 52%, frequently as a result of infection or circulatory disease. As might be expected, patients with RA also have a significant impairment in their quality of life.

The ultimate goals of treatment are the prevention or control of joint damage, the prevention of functional loss, and the relief of pain. With the introduction of the tumor necrosis factor (TNF) antagonists in 1999, the management of RA has changed markedly. Infliximab (Remicade®), etanercept (Enbrel®), and adalimumab (Humira™) are designed to modulate the inflammatory cascade of RA by binding TNF, thereby decreasing its bioavailability.

Various proinflammatory cytokines have been detected in the synovial fluid of patients with RA, including TNF, interleukin 1 (IL-1), IL-17, IL-18 and IL-6. Early studies demonstrated that in a synovial cell culture system the secondary synthesis of IL-1 and other cytokines could be markedly reduced by targeting TNF. The role of TNF is based on (1) its ability to degrade cartilage and bone in vitro, (2) its arthritogenic properties in animal models, (3) the co-localization of its receptors in RA synovium and the pannus-cartilage junction, and (4) its central role in regulating the synthesis of IL-1 in cultured RA-derived synovial cells.

Etanercept is a fusion protein consisting of the ligand-binding portion of the human p75 TNF receptor plus the Fc fragment of human IgG1. Etanercept has a terminal half-life of 102±30 hours. The recommended starting dose is 25 mg subcutaneously twice weekly, with or without methotrexate. Treatment with etanercept resulted in significant dose-related reductions in disease activity and there were no significant safety issues. TNF antagonists represent a significant advance in the therapy of active RA. They have shown efficacy in inhibiting joint destruction over various lengths of time, reducing symptoms, and improving physical function in patients with RA (Schwartzman, Fleischmann et al. 2004).

Etanercept is approved for use in the US as subcutaneous monotherapy in adults with moderate-to-severe psoriasis who are candidates for systemic therapy or phototherapy. The drug is also indicated in patients with psoriatic arthritis, in whom it may be used in combination with methotrexate. In patients with moderate-to-severe psoriasis, short-term etanercept therapy significantly increased the proportion of patients achieving a 75% reduction in the Psoriasis Area and Severity Index score compared with placebo. Similarly, in patients with psoriatic arthritis, treatment with short-term etanercept alone or in combination with methotrexate, improved clinical features of the disease, while radiographic progression of joint damage appeared to be significantly slowed (Goldsmith and Wagstaff 2005). More recently, etanercept has shown efficacy in the treatment of adults with ankylosing spondylitis (McCormack and Wellington 2004).

Because etanercept consists of the Fc domain of human IgG1, its complex with TNF is cleared from the circulation through the Fc receptor found in immune cells. Attempts to develop anti-TNF therapy based on soluble p55 TNF receptor alone are so far unsuccessful despite the fact that it binds TNF with a higher affinity as compared with the p75 TNF receptor.

Atherosclerosis is the process in which fatty substances, cholesterol, cellular waste products, calcium and fibrin form plaques in the inner lining of an artery. Plaque may block partially or totally the blood's flow through an artery. Plaque rupture is an even more serious threat, as it may cause embolism in critical narrower arteries. Atherosclerosis affects large and medium-sized arteries. The type of artery and where the plaque develops varies with each person. Atherosclerosis is a slow, progressive disease that may start in childhood. In some people, this disease progresses rapidly in their third decade. In others it doesn't become threatening until they're in their 50s or 60s. It can affect the arteries of the brain, heart, kidneys, and the arms and legs. As plaque builds up, it can cause serious diseases and complications. These include coronary artery disease, angina, heart attack, sudden death, cerebrovascular disease, stroke, transient ischemic attack and peripheral arterial disease. Diseases caused by atherosclerosis are the leading cause of illness and death in the Western world. Due to the spread of certain habits (fatty diets, tobacco abuse, and lack of exercise), cardiovascular diseases will become the major cause of declining productive years worldwide by 2020 (Murray and Lopez 1997).

In recent years, new insights into the molecular mechanisms involved in atherogenesis were generated. Brown & Goldstein were able to explain the progressive accumulation of cholesterol in plasma and arteries due to a defect of the LDL receptor,—which indeed is the primary cause of familial hypercholesterolemia (Brown and Goldstein 1986). In this complex disease, LDL-associated cholesterol (LDLc) was shown to be responsible for the accumulation of cholesterol in atherosclerotic lesions. Models for the mechanism of cholesterol accumulation in atherosclerotic plaques emphasize increased LDL uptake into the vessel wall or an increased retention of LDL that has already entered the vessel wall. At present, upregulation of liver LDL receptor expression by inhibiting cholesterol synthesis are the most effective means to lower plasma cholesterol level (Kong, Liu et al. 2006).

Lipoproteins are molecules that have a globular shape and are a combination of lipid and protein. Lipoproteins are involved in the transportation and metabolism of lipids in the body. They can be separated to atherogenic and vasoprotective lipoproteins. Atherogenic lipoproteins are generally all apoB-containing lipoproteins such as VLDL, IDL or LDL, whereas vasoprotective lipoproteins are apoA-I-containing such as HDL. The various lipoproteins consist of a hydrophobic core of triglycerides and cholesterol esters surrounded by a layer of hydrophilic free cholesterol; phospholipids; and apolipoproteins. Lipoproteins are classified by their varying buoyant density and sizes. The density of a lipoprotein particle is determined by the relative amounts of lipid and protein contained in the particle.

The following table summarizes the properties of the major lipoproteins:

| Lipoprotein Class | Density (g/mL) | Size (nm) | Major lipids | Major apolipoproteins |
|---|---|---|---|---|
| Chylomicron | 0.93 | 100-500 | Dietary TGs | B48, C-II, E |
| VLDL | 0.93-1.006 | 30-80 | Endogenous TGs | B100, C-II, E |
| IDL | 1.006-1.019 | 25-50 | CEs and TGs | B100, E |
| LDL | 1.019-1.063 | 18-28 | CEs | B100 |
| HDL | 1.063-1.210 | 5-15 | CEs | A, C-II, E |

(TG, triglycerides; CE, cholesteryl esters)

The nomenclature used for lipoproteins is purely a function of the density of each particle.

The various lipoproteins are derived from each other by a complex transformation that occurs mainly in the liver. A convenient starting point for the evolution of the lipoproteins begins with the lowest-density class, the chylomicron. These particles are synthesized in the intestinal mucosal cells directly from dietary fats, namely triglycerides, cholesterol and phospholipids, and apolipoprotein (apo) B48, which is synthesized in these cells. Their density is low because their size is large (≥100 nm) and they contain large amounts of lipid (especially buoyant triglycerides). Their large size precludes penetration of the capillary membrane. Instead, chylomicrons are secreted by intestinal mucosa into the lymphatics and then they enter the circulation through the thoracic duct. Chylomicrons acquire apoE and apoC-II in the blood. Then, they are progressively reduced in size by the action of a capillary endothelium lipoprotein lipase, which catalyzes the removal of free fatty acids from the chylomicron triglyceride pool. The depleted chylomicron remnant particle exits this pathway by its uptake into the hepatocyte through a receptor-mediated process, with the chylomicron apoE serving as the ligand for the hepatic LDL receptor. In the hepatocyte the chylomicron remnant releases its contents (i.e., the remaining triglycerides, cholesteryl esters, phospholipids, and apolipoproteins). The hepatocyte reassembles these chylomicron remnant derived products along with endogenous triglycerides and cholesteryl esters into very low-density lipoproteins (VLDLs) and secretes them into the circulation for the next phase of delivery of lipids to the periphery. Note that like chylomicrons, VLDLs are also triglyceride-rich and contain apoC-II and apoE. However, unlike chylomicrons, they contain fewer triglycerides, are smaller, and now carry apoB100 instead of apoB48.

The emergence of apoB100 here is important, in that it is a physiologic ligand for the LDL receptor. Over the next half hour, lipoprotein lipase further reduces VLDL triglyceride content, leaving the particles progressively smaller, denser, and more cholesterol-enriched as it moves down this well-known cascade to intermediate density lipoprotein (IDL). Hydrolysis of IDL triglycerides to free fatty acids is mediated by yet another lipase, hepatic lipase, and LDL soon appears as the terminal particle in this pathway. The LDL is the most cholesterol-rich lipoprotein in the plasma, and elevation of plasma LDL cholesterol (LDL-c) is a major risk factor for atherosclerosis and coronary heart disease (CHD). Thus, excessive delivery of cholesterol to the periphery by liver-derived LDL leads to atherosclerotic plaque accumulation. Therefore, LDL-cholesterol has been described, and overly simplified, as "bad cholesterol" and HDL-cholesterol as "good cholesterol." LDL, whose half-life in the circulation is on the order of several days, contains only apoB100 and essentially only one copy per particle. Note that the upstream precursor particles (IDL and VLDL) also contain apoB100. This is important because apoB levels correlate with mortality from myocardial infarction to a greater degree than do LDL levels, suggesting that the postprandial lipoproteins are also atherogenic (Tulenko and Sumner 2002).

A third type of lipoprotein, HDL, is primarily involved in returning lipids, largely cholesterol, to the liver in a process called reverse cholesterol transport.

The earliest events in atherogenesis are activation of vascular endothelial cells, adhesion, and migration of monocytes and T lymphocytes into the subendothelial space. Circulating LDL becomes atherogenic only after undergoing oxidation by vascular cells, that transform it into highly bioreactive oxidized LDL (ox-LDL). Oxidized LDL is involved in foam cell formation, and triggers proatherogenic events such as over-expression of adhesion molecules, chemoattractants, growth factors, proinflammatory and pro-apoptotic cytokines. Moreover, this toxic effect of oxidized LDL plays probably a role in plaque erosion/rupture and subsequent atherothrombosis. Several biological effects of ox-LDL are mediated through changes in the activity of transcription factors and subsequently in gene expression. Ox-LDL activates the redox-sensitive transcription factor NF-kappaB, which in turn up-regulates the expression of additional proinflammatory genes, such as genes of adhesion molecules, tissue factor, and the scavenger receptor LOX-1 (Robbesyn, Salvayre et al. 2004).

Most of the lipid-laden "foam cells" present in proatherogenic plaques are not the result of the uptake of native LDL, but rather it is due to the uptake of oxidized lipoproteins. Oxidative modification of LDL occurs in the sub-endothelial space. Uptake of ox-LDL by scavenger receptors converts monocyte-derived macrophages to foam cells. So far, at least 10 scavenger receptors have been identified, but so far, it is not known which of them contribute to this particular phenomenon in vivo, but it is clear that SRA and CD36 are quantitatively important based on knockout experiments (Kita, Kume et al. 2001).

The concentration of ox-LDL in plasma may be less than 0.5% of total LDL in CHD patients and to which the endothelial cells are exposed. This plasma concentration may not be enough for proatherogenic and proinflammatory activities of ox-LDL. Several studies have reported that remnant lipoproteins (RLP) are already oxidized in plasma. A large amount of the proatherogenic and proinflammatory lipid lysophospahtidyl choline was identified in chylomicron remnants, a constituent of RLP. In other words, major lipoproteins oxidized in plasma may be ox-RLP. The isolation method of RLP from plasma made it possible to verify the oxidative susceptibility of remnant lipoproteins and to compare the proatherogenic and proinflammatory properties of RLP with those of Ox-LDL. Similarly to ox-LDL, circulating RLP activates vascular component cells and induces several proatherogenic genes (ICAM-1, VCAM-1, HB-EGF, PDGF-A-B, COX-2, and eNOS), matrix metalloproteinases (MMPs), CD-40, CD-40L, and tissue factor (TF). Many clinical studies suggested that plasma RLP-C concentration is more convincingly associated with the increased risk of premature atherosclerosis as compared with plasma ox-LDL.

Furthermore, judging from the plasma concentration of these lipoproteins, endothelial dysfunction is more likely to be caused by circulating RLP than by circulating ox-LDL. Taken together, it is likely that reducing plasma RLP should also be the target of hyperlipidemic therapy, especially in patients with metabolic syndrome which is highly associated with plasma RLP-C level, but not with LDL-C levels (Nakajima, Nakano et al. 2006).

Apolipoprotein B is a large amphipathic protein, which exists in two forms: apoB100 and apoB48. In humans, apoB100 is expressed in the liver and is present on VLDL, IDL and LDL. ApoB48 is expressed in the intestine and is present on chylomicrons and their remnants. ApoB48 and apoB100 are encoded by the same gene. The mRNA for apoB48 is generated from the apoB100 mRNA by a so-called editing process during which a deamination of a cytidine to a uridine converts a glutamine codon to a stop codon.

The apoB100 has a pentapartite structure consisting of one globular N-terminal structure, two domains of amphipathic β-sheets and two domains of amphipathic β-helices. The N-terminal 1000 amino acid region is of vital importance for the formation of VLDL because it interacts with the microsomal triglyceride transfer protein (MTP). During the formation of lipoproteins, MTP catalyses the transfer of lipids to apoB.

The amphipathic β-sheet domains consist of antiparallel β-sheets with a width of approximately 30 Å, forming very strong lipid-binding structures. These regions are unique as compared with other apolipoproteins, preventing equilibration with different lipoproteins, but remains bound to the particle on which it was secreted into plasma. Between the two domains of amphipathic β-sheet, there is a domain of amphiphatic-helix of the type seen in the other apolipoproteins. Such a domain is also present near the C-terminus. The overall organization on the LDL has been elucidated but not completely resolved. The protein has an elongated structure encompassing the entire LDL particle. The C-terminus folds back over the preceding structure, crossing it at amino acid 3500. Here, an arginine (residue 3500) binds to a tryptophan (residue 4396), preventing the C-terminus to hinder the binding site for the LDL receptor between amino acid 3359 and 3369. Indeed, several known mutations involving these amino acids (the most well-known being that of Arg 3500) break this interaction and result in reduced binding to the LDL receptor. The C-terminal portion of the protein appears to interact with its N-terminus (Segrest, Jones et al. 2001; Olofsson and Boren 2005).

Originally identified as a component of lipoproteins in plasma, apoE contains 299 amino acid residues and has a relative molecular mass of 34,000 Da. Similar to other soluble apolipoproteins, apoE contains amphipathic β-helical lipid-binding domains that enable it to switch reversibly between a lipoprotein-bound and a lipid-free state. In the lipid-free state, apoE contains two domains, one at each end of the molecule. The two domains fold independently and each one is responsible for different key functions. The LDL-receptor-binding region is in residues 136-150. Full receptor-binding activity, however, also requires an arginine at position 172, which is located in the 'hinge region' connecting the two domains. Lipid-free apoE does not bind with high affinity to the LDL receptor. The principal lipoprotein-binding elements of apoE lie in residues 244-272 of the C-terminal domain.

ApoE is polymorphic and its various isoforms exhibit distinct functional and structural properties. The three common allelic isoforms, apoE2, apoE3 and apoE4, differ at positions 112 and 158. ApoE3, the most common isoform, contains cysteine and arginine, respectively, whereas apoE2 has two cysteines and apoE4 has two arginines at these positions. ApoE3 and apoE4 bind to LDL receptors with similarly high affinity, whereas the binding of apoE2 is 50- to 100-times weaker. As a result, homozygous apoE2 is associated with type III hyperlipoproteinemia, a lipid disorder characterized by increased plasma levels of cholesterol and triglycerides and premature cardiovascular disease.

The most pronounced pathological effect attributable to apoE polymorphism in humans is the association of apoE4 with neurodegenerative diseases, including Alzheimer's disease. Two key properties of apoE4—domain interaction and reduced stability relative to apoE2 and apoE3 have been suggested to underlie the association of apoE4 with disease. The concept of 'domain interaction' was introduced to explain why apoE3 and apoE4 differ in their lipoprotein-binding preferences. ApoE4 preferentially binds to large lower-density lipoproteins, namely VLDLs and LDLs, whereas apoE3 and apoE2 prefer smaller, cholesterol-rich high-density lipoproteins such as HDLs. The binding preference of apoE4 is governed by the presence of (positively charged) arginine at position 112. Comparison of the X-ray structures of the N-terminal domains of apoE3 and apoE4 shows that the residue at position 112 affects the conformation of the side chain of Arg61. In apoE4, Arg112 enables Arg61 in apoE4 to interact with an acidic residue in its C terminus.

The distance between the N- and C-terminal domains of lipid-free apoE differ owing to inter-domain interaction. Domain interaction has been implicated in the production of neurotoxic fragments when neurons are stressed and induced to express apoE4. In addition to killing neurons, these fragments generate intracellular deposits resembling neurofibrillary tangles that, along with amyloid plaques, are pathological hallmarks of Alzheimer's disease. Partially folded or molten-globule-like conformations give proteins flexibility and adaptability for the substantial conformational changes that accompany ligand binding. In particular, variation in the stability of the N-terminal domains of the three apoE isoforms might contribute to their differences in lipoprotein-binding preferences and other biological functions in vivo. The lower stability of apoE4 relative to apoE3 could also have an important pathological role in the brain.

Heterogeneity in the structure near the LDL-receptor-binding region of lipoprotein-bound apoE has been detected with monoclonal antibodies against specific epitopes. On binding to phospholipids, apoE undergoes a considerable conformational change. Recent studies suggest that phospholipid-bound apoE folds into an α-helical hairpin-like structure. An α-helical hairpin conformation puts all of the known elements of the LDL-receptor-binding motif, including Arg172, into a structural apex, which potentially explains why only lipid-bound apoE binds to the LDL receptor with high affinity. The presence of a phospholipid bilayer in apoE-containing lipoprotein particles, however, has not been experimentally verified (Hatters, Peters-Libeu et al. 2006).

LDLR was first discovered in 1974. Since then, its structure, function, mutants, and physiological as well as pharmacological modulations have been extensively studied. LDLR on the cell surface binds and internalizes apoB- and apoE-containing lipoproteins from the circulation. The affinity of LDLR for apoE3 and E4-lipoproteins (KD=0.12 nM) is 25-50 fold higher than for apoB lipoproteins. Yet, apoE-containing chylomicron remnants have additional entry modes into hepatocytes. After endocytosis, the LDLR uncouples from its ligand and returns to the cell surface for recycling, while the LDL undergoes further metabolism (Kong, Liu et al. 2006).

The human LDLR is a membrane-spanning glycoprotein with a highly conserved structure in human and other animal species. Its mature form contains 836 amino acid residues with a molecular mass of 160 kDa, and has five functional domains: a ligand-binding domain, an epidermal growth factor (EGF) precursor homology domain, an O-linked polysaccharide domain, a membrane-spanning domain, and a short cytoplasmic domain. Analysis of the oligosaccharide contents of LDLR revealed one Asn-linked oligosaccharide and 6-9 O-linked units (Cummings, Kornfeld et al. 1983). The position of the single Asn-linked oligosaccharide is amino acid residue 657 of the human LDLR precursor (Zhang, Li et al. 2003).

The ligand-binding domain of LDLR consists of seven cysteine-rich imperfect repeats (R1-R7) of ~40 amino acids, the so-called LDLR class A repeats (LDL-A, also known as complement-type repeats). Nuclear magnetic resonance structures as well as the crystal structure revealed a two-loop conformation stabilized by three disulfide bonds. Characteristically, disulfide bond formation occurs between cysteine residues I and III, II and V, and IV and VI (Roman numerals indicate the relative position of the cysteine residues in the repeat). In addition, a conserved sequence of acidic amino acids (CDXXXDCXDXSDE; acidic residues indicated in bold and X representing any amino acid) is present in the C-terminal part of each LDL-A repeat. Crystallographic analysis demonstrated that many acidic residues were involved in coordination complexing of a calcium ion, explaining the calcium requirement for correct folding and disulfide bond formation of LDL-A repeats and for binding of lipoproteins to LDLR. The structural requirements for binding LDL and VLDL differ: LDL binds its receptor via apoB100, VLDL via apoE. Whereas LDL binding depends on the presence of R2-R7, only R5 appears essential for interaction with VLDL. The importance of R5 is underscored by the high number of FH mutations that have been localized to this repeat. Only a minor number of FH mutations locate to R1, which is not important for binding of either ligand to the LDLR (Gent and Braakman 2004).

The very-low-density lipoprotein (VLDL) receptor (VLDLR) is remarkably similar to LDLR. The major difference is the presence of one extra complement-type repeat in the ligand binding domain present at the N terminus. In contrast to LDLR, the majority of VLDLR is expressed in extra-hepatic tissues, e.g. heart, muscle, and adipose tissue. VLDLR functions in the uptake of triglyceride-rich, apoE-containing lipoproteins (Hussain, Strickland et al. 1999).

The human apoE receptor 2, or LR7/8B, contains seven ligand binding repeats, grouped as 5 C2 separated by a linker, similar to that found in VLDLR (5 C3) and different from that observed in LDLR (4 C3). The apoE receptor 2 is closer to VLDLR than to LDLR and therefore it is expected to have broad ligand binding ability, similar to that observed for VLDLR, rather than the restricted specificity observed for LDLR (Hussain, Strickland et al. 1999).

Megalin (also known as gp330 or LRP-2) is a single polypeptide of 4660 amino acids containing 36 cysteine-rich ligand binding domains, 16 EGF precursor homology domains, and 40YWTD repeats in the extracellular domain. There are four clusters of ligand binding domains consisting of 7, 8, 10, and 11 complement-type repeats in the molecule that recognize several groups of ligands (Hussain, Strickland et al. 1999). Other members of the LDLR family include the LDLR-related protein, LR11 (also termed SORLA-1), LRP3 and LRP6. Their exact ligand-binding specificity is only partially known (Hussain, Strickland et al. 1999).

Members of the LDLR family recognize several structurally dissimilar ligands. LDLR and apoE receptor 2 bind lipoproteins and lipoprotein lipase. LDLR can distinguish between the three isoforms of apoE with binding affinities in the order of apoE4>apoE3>>>apoE2. The dissociation constant (KD) of ApoE4 and 3 lipoproteins is 0.12 nM, whereas apoE4 has very low affinity for LDLR. However, other receptors in the family do not discriminate and all of them seem to bind equally all isoforms of apoE. Nevertheless homozygous ApoE2 individuals (about 1% of the population (Mahley 1988)) exhibit a ~2 fold higher VLDL triglycerides due to ineffective uptake of VLDL through the LDL receptor (Cardona, Tinahones et al. 2003). Other members of the LDLR family are less specific and bind lipoproteins as well as various proteases and protease inhibitors. In addition to overlapping ligand specificities, each receptor appears to have a unique ligand. ApoB100 has been shown to bind to the LDLR and to megalin. A monoclonal antibody that inhibited the binding to megalin of RAP, apoE-VLDL, lipoprotein lipase, aprotinin, and lactoferrin recognized complement-type repeats 4 and 5 within domain 2 (amino acids 1111-1210), indicating that this is the common binding site of these four ligands. An arrangement of seven complement repeats and EGF precursor regions similar to LDLR is also present in megalin. Other receptors contain eight complement-type repeats in their ligand binding domains. The presence of the eight repeats may prevent the binding of a larger LDL to these receptors. Receptor Associated Protein (RAP), a chaperone present in the lumen of the endoplasmic reticulum, binds to all members of the LDLR family. It assists in the proper folding and in preventing premature binding of ligands to the receptor. A remarkable property of RAP is that it acts as a universal antagonist for the binding of all the ligands to different receptors (Hussain, Strickland et al. 1999).

The liver is not only the source of circulating LDL (via VLDL) but also is the major site of LDL catabolism. LDL uptake by the liver is mediated largely by receptor-dependent mechanisms involving the low-density lipoprotein receptor (LDLR) and fully 80 to 90% of whole body receptor-dependent LDL uptake occurs in the liver (Spady 1992). Also the large HDL-containing apoE particles can deliver cholesterol to the liver directly because they contain apoE, which exhibits high affinity for the LDLR (Hatters, Peters-Libeu et al. 2006). On a Western diet, humans synthesize 1 g cholesterol/day and ingest additional 0.4 g (Grundy 1983). At steady state, this amount of cholesterol must also be removed. The various lipoproteins, receptors and enzymes involved in cholesterol traffic and metabolism are tuned to cope with this level of "excess" cholesterol. Any interference in the level or activity of these lipoproteins, receptors or enzymes leads to change in the levels of serum cholesterol.

The expression level of LDLR is indirectly regulated at the transcriptional level by cytoplasmic cholesterol. The LDLR promoter consists of 200 base pairs upstream of the translation initiation codon. The promoter contains a sterol regulatory element 1 (SRE-1), flanked by two Sp1 binding sequences. Basal expression of LDLR is mediated by the two Sp1 elements. Expression of LDLR may be synergistically enhanced upon binding of nuclear sterol regulatory element binding proteins (nSREBPs) to the SRE-1 of the LDLR promoter. nSREBPs belong to the large family of basic helix-loop-helix-leucine zipper (bHLH-Zip) transcription factors. Three members of the nSREBP family, nSREBP-1a, -1c, and -2, have been identified. They are synthesized in the ER as inactive precursors termed SREBP. Their NH2-terminal domain protrudes into the cytosol. It contains the bHLH-Zip and an acidic domain that has to bind a transcription co-activator to function. The central portion of SREBP consists of two membrane-spanning domains that anchor SREBP to the ER and the nuclear envelope. The COOH terminal segment also extends into the cytosol and serves as the regulatory domain for the transformation of SREBP into active nSREBP.

Three ER membrane proteins participate in regulation of SREBP processing. When cellular cholesterol is abundant, it binds to a transmembrane escort protein termed SREBP cleavage activation protein (SCAP), which together with one of two other proteins termed Insulin Induced Gene -1 and -2 (Insig-1 and Insig-2) forms a SREBP/SCAP/Insig ternary complex. This complex is trapped in the ER membrane, thereby preventing the processing of SREBP.

Depletion of cytoplasmic cholesterol destabilizes the ternary complex, which dissociates to form SCAP-SREBP heterodimers. These heterodimers are transported to the Golgi apparatus, where SREBPs are cleaved proteolytically to generate active nSREBPs. These nSREBPs and particularly nSREBP-2 translocate to the nucleus and bind and activate the LDLR promoter, as well as about 30 other genes involved in lipid metabolism. The nSREBPs are not stable. They are polyubiquitinated and rapidly degraded by the proteasome with an estimated half-life of 3 h.

Thus, when cholesterol or its derivatives are abundant in cells, the SREBP pathway is suppressed, and the transcription of the LDLR gene is maintained at a very low level. In contrast, cholesterol deficiency promotes LDLR expression (Kong, Liu et al. 2006). These mechanisms occur in all cell types, including hepatocytes, leading to an undesired reduction of liver LDLR expression when serum cholesterol (LDL-c) is abundant.

The liver is capable of cholesterol catabolism and conversion of cholesterol into bile salts, which are secreted to the intestine. Yet most of the bile salts are effectively reabsorbed. The liver expresses cholesterol-7α-hydroxylase, which catalyses the first and rate-limiting step of a complex enzymatic cascade in which the steroid nucleus of cholesterol is hydroxylated in two or three positions and the side chain of cholesterol is shortened and carboxylated. The end products are molecules called bile salts. One of the two bile salts produced in the livers of humans is called cholate. Unlike cholesterol, which is highly insoluble in water, bile salts are water-soluble detergent-like molecules.

Hepatocytes are polarized liver cells that create a boundary between blood on one side and bile on the other side; the sinusoidal membrane faces the blood and the canalicular membrane faces the bile. There are three main transporters on the canalicular membrane. ABCB11 is responsible for the ATP-dependent transport of bile salts into bile. Once present in bile, bile salts turn around and interact with the canalicular membrane and the transporters ABCB4 and ABCG5/G8. This complex interaction leads to the formation of a biliary micelle. The daily secretion rates for the biliary lipids range up to 2 g/day for cholesterol, 11 g/day for phosholipids, and 24 g/day for bile salts. Yet, bile salts are synthesized at a rate of only 0.4 g/day in the average individual because, once they have completed their functions in the biliary tree and intestine, almost all are reabsorbed in the distal ileum and returned to the liver through portal venous circulation. Less than 5% of bile salts are lost in the feces each day, which amounts to about 0.4 g/day. Considering that cholesterol is the substrate for bile salt synthesis in the liver, a loss of 0.4 g/day of bile salts translates to a loss of the same quantity of cholesterol. (Carey M C, Duane W C. Enterohepatic circulation. In: Arias I M, Boyer J L, Faustoet N, et al., eds. The Liver: Biology and Pathobiology. New York: Raven Press, 1994:719-767). Cholesterol is secreted into bile at the rate of up to 2 g/day. The average American diet consists of about 0.4 g/day of cholesterol. Therefore, the amount of cholesterol that is derived from bile in the intestine is up to 5-fold in excess of the amount that is taken in through the diet. The average individual absorbs 50% of the cholesterol that passes through the intestine each day. This means that 50% is lost in the feces, amounting to 1.2 g/day. Together, 1.6 g of cholesterol is normally removed in feces, of which 1.2 g originate in the liver.

Bile acid sequestrants such as Cholestipol™ are effective LDLc lowering drugs with large clinical experience. They decrease LDLc from 10 to 30% in a dose-dependent manner, but with frequent side effects that limit their use in many cases. Colesevelam is a new, more potent bile acid sequestrant that is available in 625 mg tablets; the recommended dose in adults is 3.8 g per day (three tablets twice daily with meals) and is better tolerated than the less potent bile acid sequestrants, colestyramine and Colestipol™. Because of their good safety profile, new resins remain as alternative to statins in monotherapy, especially in children or young women.

Ezetimibe is a new lipid-lowering drug that inhibits the intestinal absorption of cholesterol from dietary and biliary sources by impeding the transport of cholesterol across the intestinal wall. Used as monotherapy, ezetimibe decreases LDLc by a mean of 17.3%. The addition of ezetimibe 10 mg per day to ongoing statin therapy provides further reduction in LDLc levels (−14 to −25%) compared to placebo. This regimen is generally well tolerated across a wide dose range of different statins, and offers a new approach to LDLc reduction, avoiding high doses of statins, or allowing reductions over 60% in LDLc when used with a potent statin to reach LDLc goals in high risk patients (Civeira 2004).

Familial hypercholesterolemia (FH) is an autosomal codominant inherited disorder of lipoprotein metabolism characterized by very high plasma concentrations of low density lipoprotein cholesterol (LDLc), tendon xanthomas and increased risk of premature coronary heart disease (CHD). Usually, clinically identified FH is caused by mutations in the LDL receptor gene (LDLR). The heterozygote of FH is one of the most common autosomal dominant genetic diseases in humans, whereas the homozygote is rare but more severe. The frequency of heterozygotes is approximately one in 500 individuals in most countries. However, some populations around the world such as French Canadians, Afrikaners in South Africa, Lebanese and Finns have a much higher prevalence due to a founder effect. It has been estimated that there are 10,000,000 people with FH worldwide. FH is a world public health problem due to the high incidence of premature (<55 years in men and <65 years in women) cardiovascular disease, mainly CHD, and to the reduction in the life expectancy observed in many families with FH. Approximately, 85% of males and 50% of females will suffer a coronary event before 65 years old if they are not treated. Up to 9% of the total premature CHD in eastern Finland and Germany is associated with FH (Civeira 2004).

More than 800 mutations have been reported to date to cause FH, and they have been divided into several classes based on their phenotypic effects on the protein (Kong, Liu et al. 2006). The penetrance of FH is almost 100%, meaning that half of the offspring of an affected parent have a severely elevated plasma cholesterol level from birth onwards, with males and females equally affected. Elevated plasma LDL levels result from slower LDL catabolism and a paradoxical lipoprotein overproduction. LDLc in untreated heterozygous FH (heFH) subjects is typically in the range of 190-400 mg/dl (4.9-10.3 mmol/l). Similarly, mouse LDLR (−/−) hepatocytes secrete apoB100 at a 3.5-fold higher rate than do wild-type hepatocytes. Furthermore, in LDLR (−/−) cells, less than 20% of newly synthesized apoB is degraded as compared with 55% in wild-type hepatocytes. Thus, a functional liver LDLR is critical in reducing circulating LDL (Twisk, Gillian-Daniel et al. 2000). Considering that <100 mg/dl (2.6 mmol/l) is the optimal LDLc concentration as defined by the Third Report of the National Cholesterol Education Program Adult Treatment Panel (NCEP-ATPIII) guidelines, it would be necessary to achieve mean reductions between 50 and 75% in heFH patients to reach that goal. Lifestyle modification should always be instituted but is unlikely to result in acceptable LDLc levels. An LDLc<100 mg/dl (2.6 mmol/l) remains the optimal level and goal for those subjects with symptomatic CVD (Civeira 2004). Thus, combination of several means to reduce serum LDLc is required, especially for FH patients.

Current treatments for heFH include (www.emedicine.com/med/TOPIC1072):

A diet that severely limits saturated fats, trans fats, and cholesterol. Desirable weight should be attained. Significant weight loss should improve all lipid parameters (LDLc, HDLc, triglycerides).

Aerobic and toning exercises improve blood lipid levels if performed for longer than 30 minutes, 4 or more days per week.

Because doubling the dose of any HMG-CoA reductase inhibitor lowers the LDLc only by 6-7%, a combination of different cholesterol-lowering medications is more effective. Such a combination should include a high dose of one of the three strongest statins and one or more other LDL lowering medications such as bile acid sequestrants, ezetimibe, or niacin. To decrease the risk of myopathy, one step below the maximum dose of the statin should be considered. Adding a third or even fourth agent is beneficial. With 50% functional LDL receptors, heterozygous FH patients have an excellent response to the usual cholesterol-lowering drugs, but treatment still remains difficult. Estrogen replacement therapy in postmenopausal women also helps lower LDLc levels, but this therapy is not recommended because of its adverse effects in older women, although the benefits may sometimes outweigh risks.

Patients with documented CHD whose LDLc level cannot be lowered below 200 mg/dL by conventional therapy are candidates for LDL apheresis. Patients without CHD but with an LDLc level of higher than 300 mg/dL also qualify for this intervention. However, health insurance coverage is not automatic, and decisions are made on a case-by-case basis because of the costs, which approach $3000 for each treatment, every 2 weeks, for the patient's lifetime.

The C-type lectins represent a large family of ca2+-dependent lectins that share primary structural homology in their carbohydrate-recognition domains. This very large family, which includes many endocytic receptors, many proteoglycans, and all known collectins and selectins, is found throughout the animal kingdom. Most of the members of this family differ, however, with respect to the types of carbohydrate structures that they recognize with high affinity.

The first lectin identified in animals was the hepatic asialoglycoprotein receptor or the hepatic Gal/GalNAc receptor. Desialylated glycoproteins are removed much more rapidly from the circulation than the parent glycoproteins. In addition, the penultimate galactose residues exposed upon desialylation are critical for clearance. The asialoglycoproteins removed from the circulation are sequestered in the liver and principally in lysosomes. A specific Ca2+-dependent receptor for asialoglycoproteins was identified in hepatocyte plasma membrane fractions. The hepatic lectin binds to glycoproteins containing either nonreducing terminal GalNAc or galactose.

All Ca2+-dependent lectins share a common structural motif. The sequence homology was noted in the CRD, and proteins with this motif are classified as members of the C-type lectin family. The discovery of the CRD for the C-type lectins opened the way to characterize other related proteins that also displayed Ca2+-dependent binding to carbohydrate ligands. To date, more than 20 different proteins containing a C-type lectin CRD have been identified in humans and corresponding homologues were also found in many other higher animals. These many C-type lectins in higher animals are classified into subfamilies, based on their function or unique localization.

The hepatic lectins represent a class of C-type lectins capable of mediating endocytosis of bound ligands. The endocytic pathway involves lectin recognition of ligands at the cell surface, internalization via coated pits, and delivery of the complex to endosomal compartments where the low pH induces dissociation of ligand and lectin. The lectins recycle to the cell surface and repeat the process (Essentials of Glycobiology, Varki A. et al, Cold Spring Harbor Laboratory Press, Cold Spring Harbor, N.Y.).

One of the well-known and thoroughly studied C-type lectin in mammals is the asialoglycoprotein receptor (ASGP-R) uniquely found on hepatocytes. This high capacity receptor binds ligands with terminal galactose or N-acetylgalactosamine (GalNAc) and routes these to lysosomes before recycling to the cell surface. Natural ligands for the ASGP-R are believed to be serum glycoproteins that lose their terminal sialic acid during circulation, exposing clusters of subterminal Gal residues on their N-glycans. Thereby, the ASGP-R is believed to be primarily involved in maintaining the serum concentration of structurally diverse glycoproteins.

More recently, it was found that the ASGP-R rapidly clears the less abundant family of glyproteins whose N-glycans terminate with sialylated GalNAc, whereas the majority of the glycoproteins whose N-glycans terminate with sialylated Gal are mainly cleared following removal of the terminal sialic acid by the galactose particle receptor present on liver Kupffer cells. Indeed, the affinity of ASGP-R to N-glycans terminating with GalNAc is approximately 50-fold higher than for those terminating with Gal.

The art teaches how to generate recombinant glycoproteins whose terminal saccharide residue is GalNAc rather than Gal. Thus, stable transfection of CHO lec8 cells, which lack a functional UDP-Gal transporter, with βGalNAc transferase (βGalNAcT) results in expression of glycoproteins whose N-glycans are triantennary, tetraantennary and even higher structures having penultimate βGalNAc instead of βGal (Kawar, Haslam et al. 2005). Such CHO cells may be used instead of the regular CHO cells for expression of recombinant glycoproteins carrying a penultimate βGalNAc.

The ASGP-R is highly abundant on hepatocytes, which carry 150,000-500,000 binding sites/cell. The number of hepatocytes present in the liver is about $2 \times 10^8$ per mouse and the rate of ASGP-R internalization is 0.1 pmol/min per $10^6$ cells. On the basis of such estimates, the mouse liver is capable of removing about 1.2 nmol/h of ligand through the ASGP-R, or the equivalent of 2.4 μg/h of a glycoprotein with a molecular weight of 20,000 Da (Park, Mi et al. 2005). Extrapolation to a human liver suggests an almost unlimited potential clearance rate of over 5 mg/h or 120 mg/day. In case of a protein of molecular weight of $2 \times 10^6$ Da, these values will increase to 5 g/h or 120 g/day.

Several approaches were developed for reducing serum LDL based on the liver ASGP-R. One approach was based on the synthesis of a glycolipid containing terminal GalNAc residues. The idea was that the hydrophobic component of the glycolipid, a long-chain fatty acid, will rapidly and irreversibly penetrate into LDL particles, thereby enabling their binding to the liver ASGP-R and their subsequent internalization. Although this glycolipid did not show signs of acute toxicity, it does not exhibit specificity for LDL and in fact could bind to HDL and to any cytoplasmic membrane. Furthermore, its overall detergent-like structure raises the risk of long-term toxicity. Nevertheless, this study was a proof of principle, as ~30% reduction of serum cholesterol was observed, suggesting that the ASGP-R route is feasible (Rensen, van Leeuwen et al. 2004; Rensen, Sliedregt et al. 2006).

In an earlier study, a more LDL-specific approach was employed, using Fab fragment of antibodies directed against human LDL. Lactose was coupled to these Fab fragments by reductive amination with sodium cyanoborohydride and clearance of radiolabelled human LDL was demonstrated in rats (Bernini, Tanenbaum et al. 1986). This approach is limited by the use of antibodies or their Fab fragments, which by themselves could be immunogenic, leading to formation of antiidiotypic antibodies, especially when administered regularly in the rather large quantities required for binding to serum LDL.

An alternative approach for transporting a selected substance present in extracellular fluids, such as blood or lymph, into cells is provided in U.S. Pat. No. 6,858,578, issued Feb. 22, 2005. According to one example of U.S. Pat. No. 6,858,578, a chimera comprising a soluble LDLR and transferrin is generated and used for uptake of LDL into cells. While this approach is feasible, it does not direct LDL specifically to the liver. The transferrin receptor is expressed in most cell types and in all organs. Excess cholesterol entering into most cells will be secreted back to the circulation. Thus, there is still a need to direct excess cholesterol specifically to the liver, where it can be metabolized into bile acids and secreted to the digestive tract.

U.S. Pat. Nos. 5,958,408 (Griffiths, et al, Sep. 28, 1999) and 5,965,131 (Griffiths, et al, Oct. 12, 1999) describe delivery of diagnostic and therapeutic agents to a target site. According to these inventions, a "direct targeting species" is a diagnostic or therapeutic agent coupled to a protein. Said protein, e.g., tumor-specific antibody directs said agent to the target tissue. A "clearing agent" is provided, which is a specific binding complement to the direct targeting species. Examples of said clearing agents are anti-idiotipic antibodies. In one embodiment of the invention, the clearing agent is conjugated to galactose, which binds to the hepatic asialoglycoprotein receptor, whereby the clearing agent and clearing agent-primary targeting species complexes are rapidly recognized by liver hepatocytes. The idea is to remove excess therapeutic agent or excess diagnostic agent that was administered to the patient, thereby obtaining improved binding specificity of these agents to their target tissues.

Oxidized LDL is the major proatherogenic lipoprotein. Unlike its parental LDL, it does not bind to LDLR and hence it is not cleared by hepatic uptake. Extensive studies using oxLDL as a representative ligand disclosed at least 11 different receptors, which are collectively categorized as "scavenger receptor family". Advanced glycation end products (AGE) and their receptor systems have been studied independently until recent findings that AGE-proteins are also recognized as active ligands by the same scavenger receptors. These receptors belong to several sub families, including class A scavenger receptors (SR-A), class B scavenger receptors such as CD36 and SR-BI, type D scavenger receptor (OLR1/LOX1) and FEEL-1/FEEL-2. Endocytic uptake of OxLDL and AGE-proteins by macrophages or macrophage-derived cells is mainly mediated by SR-A and CD36 (Horiuchi, Sakamoto et al. 2003). SR-A is a trans-membrane glycoprotein expressed on macrophages. Its precursor consists of 451 amino acid residues of which the N-terminal 50 are cytoplasmic, followed by 26 membrane-spanning residues and 375 residues cat the extracellular domain. The extracellular domain includes 7 potential N-glycosylation sites.

OLR-1/LOX-1 is a C-type lectin receptor, involved in hepatic clearance of plasma oxLDL and AGE-proteins. It is a single pass trans-membrane glycoprotein of a monomeric molecular weight of 40 kDa, but is present as a 80 kDa dimer through a disulfide bond at Cys 140 (Xie, Matsunaga et al. 2004). The OLR1/LOX-1 precursor consists of 273 amino acid residues, of which 216 C-terminal residues are the extracellular region, which contains the ligand-binding domain. It is expressed in vascular endothelium and vascular-rich organs such as lungs, spinal cord and bone marrow. (Sawamura, Kume et al. 1997). The extracellular residues 73 and 139 are potential N-glycosylation sites (Shi, Niimi et al. 2001). It mediates the recognition, internalization and degradation of oxLDL by vascular endothelial cells and macrophages.

A soluble form of OLR1/LOX-1 was identified in culture media of aortic endothelial cells. It was generated by proteolytic shedding of the membrane-associated receptor through cleavage past either Arg86 or Lys89 (Murase, Kume et al. 2000). Preliminary studies failed to show binding of soluble OLR1/LOX-1 to oxLDL (Murase, Kume et al. 2000). However, this could be due to the loss of an essential N-glycan at residue 73 since it was demonstrated than glycosylation was essential for ligand binding to membrane-associated OLR1/LOX-1 (Kataoka, Kume et al. 2000). However, more recently a soluble receptor corresponding to the ligand-binding domain of OLR1/LOX-1 inhibited uptake oxLDL to endothelial cells (Smirnova, Sawamura et al. 2004).

Soluble receptors or binding proteins were proposed as means to neutralize and inhibit the action of various cytokines. However, because of its larger size, the resulting cytokine-soluble receptor complex has a longer half-life in the circulation as compared with its individual constituents. Furthermore, the formation of the complex is reversible and hence it may serve as a long-acting source of the cytokine. Thus, there is a need to provide means for rapid clearance of complexes formed between soluble receptors and their ligands.

SUMMARY OF THE INVENTION

In one aspect, the invention relates to a glycan-modified soluble receptor or binding protein of a cytokine, growth factor, lipoprotein or oxidized lipoprotein, such as a soluble receptor of the TNF receptor superfamily; a soluble LDL receptor or a related homolog; a soluble scavenger receptor; a soluble OLR1/LOX-1, and soluble FLk-1, which was modified to carry a terminal Gal, GlcNAc or GalNAc.

Examples of the glycan-modified soluble receptor or binding protein include, but are not limited to, asialylayed soluble TNFR (as-sTNFR), asialo, agalacto soluble TNFR (as-ag-sTNFR), lactosaminated soluble TNFR (lac-sTNFR), N-acetylgalactosaminated soluble TNFR (sTNFR-Gn), N-acetyl galactosaminated soluble LDLR (sLDLR-Gn), N-acetyl galactosaminated soluble OLR1/LOX-1 (sOLR1/LOX-1-Gn), and lactosaminated soluble FLk-1 (lac-sFLK-1).

In another aspect, the invention relates to the use of a glycan-modified soluble receptor or binding protein of the invention in the manufacture of a medicament for facilitating the clearance of a circulating cytokine, growth factor, lipoprotein or oxidized lipoprotein capable of binding said soluble receptor or binding protein.

In one embodiment of the invention, the lipoprotein or oxidized lipoprotein can be LDL, VLDL, oxidized LDL or a remnant lipoprotein.

In a further embodiment of the invention, the cytokine or growth factor can be IL-1α, IL-1β, IL-2, IL-3, IL-4/IL-13, IL-5, IL-7, IL-9, IL-10, IL-12, IL-14, IL-15, IL-17, IL-18, IL-19, IL-20, IL-21, IL-22, IL-23, IL-24, IL-25, IL-26, IL-28A, IL-28B, IL-29, activin, apo2L/TRAIL, APRIL, BAFF, TNFSF9, BMP-2, CD27L, BMP-3, BMP-7, CD30L, CD40L, CNTF, EGF, VEGF, FASL, FGF, CSF, FLT3, G-CSF, GDNF, GITRL, GM-CSF, GH, HGF, IGF I & II, IFN-α, IFN-γ, LIGHT, lymphotoxin, M-CSF, MSP, NGF, NT-3, NT-4, OX-40L, PDGF, Prolactin, SCF, TGF-α, TGF-β, TPO, TRANCE, TSLP and TWEAK.

In another aspect, the invention relates to the use of a glycan-modified soluble receptor or binding protein of the invention, in the manufacture of a medicament for treating or preventing a disease or a disorder or condition whose pathogenesis or course is associated with the levels and/or activity of a cytokine, growth factor, lipoprotein or oxidized lipoprotein.

In one embodiment of the invention, the pathogenesis or course of the disease, disorder or condition is associated with excess of a lipoprotein or oxidized lipoprotein such as LDL, VLDL, oxidized LDL, and remnant lipoprotein, in the circulation.

In a further embodiment of the invention, the disorder is hypercholesterolemia.

In another further embodiment of the invention, the pathogenesis or course of the disease disorder or condition is associated with the levels or activity of a cytokine or growth factor or selected from, IL-1α, IL-1β, IL-2, IL-3, IL-4/IL-13, IL-5, IL-7, IL-9, IL-10, IL-12, IL-14, IL-15, IL-17, IL-18, IL-19, IL-20, IL-21, IL-22, IL-23, IL-24, IL-25, IL-26, IL-28A, IL-28B, IL-29, activin, apo2L/TRAIL, APRIL, BAFF, TNFSF9, BMP-2, CD27L, BMP-3, BMP-7, CD30L, CD40L, CNTF, EGF, VEGF, FASL, FGF, CSF, FLT3, G-CSF, GDNF, GITRL, GM-CSF, GH, HGF, IGF I & II, IFN-α, IFN-γ, LIGHT, lymphotoxin, M-CSF, MSP, NGF, NT-3, NT-4, OX-40L, PDGF, Prolactin, SCF, TGF-α, TGF-β, TPO, TRANCE, TSLP and TWEAK.

In another further embodiment of the invention, the pathogenesis or course of the disease, disorder or condition is exacerbated by excess of a growth factor or wherein the course of the disease disorder or condition is ameliorated by reducing the levels of a growth factor.

In another further embodiment of the invention, the disease is cancer.

An additional aspect of the invention relates to the use of a glycan-modified soluble TNF receptor (sTNFR) carrying a terminal Gal, GlcNAc or GalNAc in the manufacture of a medicament for treating or preventing a disease or disorder or condition whose pathogenesis or course is associated with the levels or activity of TNF.

Examples of a disease or disorder or condition whose pathogenesis or course is associated with the levels or activity of TNF include, but are not limited to, inflammatory diseases, autoimmune diseases, e.g. rheumatoid arthritis, Crohn's disease and psoriasis.

In one embodiment of the invention, sTNFR is as-sTNFR, as-ag-sTNFR, lac-sTNFR, and/or sTNFR-Gn.

In a further embodiment of the invention, the sTNFR is sTNFRp55.

Also, another aspect of the invention relates to the use of a glycan-modified soluble LDL receptor (sLDLR) or its related homologous carrying a terminal Gal, GlcNAc or GalNAc in the manufacture of a medicament for treating hypercholesterolemia.

In one embodiment of the invention, the medicament is for treating familial hypercholesterolemia.

In a further embodiment of the invention, the soluble receptor is sLDLR-Gn.

A further aspect of the invention relates to the use of a glycan-modified soluble OLR1/LOX-1 carrying a terminal Gal, GlcNAc or GalNAc in the manufacture of a medicament for treating or preventing atherosclerosis in an individual.

In one embodiment of the invention, the individual is at high risk of contracting atherosclerosis.

In another embodiment of the invention the soluble receptor is sOLR1/LOX-1-Gn.

A further aspect of the invention relates to the use of a glycan-modified soluble FLk-1 carrying a terminal Gal, GlcNAc or GalNAc in the manufacture of a medicament for the treatment of primary cancer or metastasis.

In one embodiment of the invention the soluble receptor is lactosaminated soluble FLk-1 (lac-sFLK-1).

It is one object of the invention to provide a pharmaceutical composition comprising a glycan-modified soluble receptor of the invention and a pharmaceutically acceptable carrier for facilitating the clearance of a circulating cytokine, growth factor, lipoprotein or oxidized lipoprotein.

The invention provides a pharmaceutical composition comprising a pharmaceutically acceptable carrier and a glycan-modified soluble receptor selected from a soluble asialo TNFR (as-sTNFR), asialo, agalacto soluble TNFR (as-ag-sTNFR), lactosaminated soluble TNFR (lac-sTNFR), N-acetylgalactosaminated soluble TNFR (sTNFR-Gn), N-acetyl galactosaminated soluble LDLR (sLDLR-Gn), N-acetyl galactosaminated soluble OLR1/LOX-1 (sOLR1/LOX-1-Gn), and lactosaminated soluble FLk-1 (lac-sFLK-1) for facilitating the clearance of a circulating cytokine, growth factor, lipoprotein or oxidized lipoprotein.

It is another object of the invention to provide a method for facilitating the clearance of a circulating cytokine, growth factor, lipoprotein or oxidized lipoprotein, comprising administering to a subject in need a therapeutically effective amount of a glycan-modified soluble receptor or binding protein of the invention.

It is a further object of the invention to provide a method for treating or preventing a disease or disorder or condition whose pathogenesis or course is associated with the levels and/or activity of a cytokine, growth factor, lipoprotein or oxidized lipoprotein, comprising administering to a subject in need a therapeutically effective amount of a glycan-modified soluble receptor or binding protein of the invention.

Also, the invention provides a method for treating or preventing a disease disorder or condition whose pathogenesis or course is associated with the levels or activity of TNF, comprising administering to a subject in need a therapeutically effective amount of glycan-modified soluble TNF receptor (sTNFR) carrying a terminal Gal, GlcNAc or GalNAc.

In addition, the invention provides a method for treating or preventing hypercholesterolemia, comprising administering to a subject in need a therapeutically effective amount of a glycan-modified soluble LDL receptor (sLDLR) or its related homologous carrying a terminal Gal, GlcNAc or GalNAc.

Furthermore, the invention provides a method for treating or preventing atherosclerosis, comprising administering to a subject in need a therapeutically effective amount of a glycan-modified soluble OLR1/LOX-1 carrying a terminal Gal, GlcNAc or GalNAc.

Additionally, the invention provides a method for treating primary cancer or metastasis, comprising administering to a subject in need a therapeutically effective amount of a glycan-modified soluble FLk-1 carrying a terminal Gal, GlcNAc or GalNAc.

DETAILED DESCRIPTION OF THE INVENTION

Figure 1:
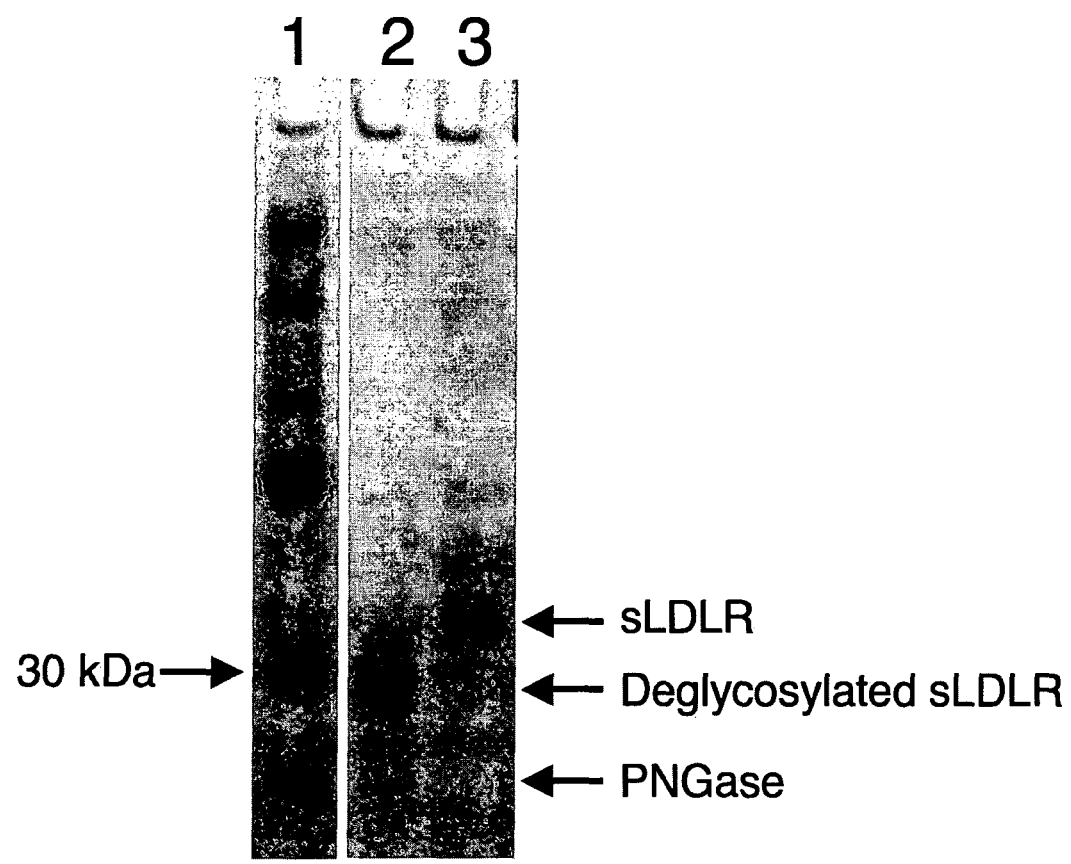
FIG. 1 shows SDS-PAGE of sLDLR expressed in CHO cells before and after treatment with PNGase (also known as N-Glycosidase F, an amidase that cleaves between the innermost GlcNAc and asparagine residues of high mannose, hybrid and complex oligosaccharides from N-linked glycoproteins). The samples were run on a gradient gel and stained with coomassie blue.

In one aspect, the invention relates to a glycan-modified soluble receptor or binding protein, carrying a terminal Gal, GlcNAc or GalNAc and to its use for facilitating the rapid clearance of a circulating undesired component capable of binding said soluble receptor or binding protein.

The term soluble receptors and binding proteins relate to circulating and artificial proteins that bind with high affinity and specificity to various cytokines, growth factors, polypeptide hormones and other circulating effector proteins. The term binding proteins according to the invention excludes antibodies and fragments thereof. A soluble receptor includes the extracellular, ligand-binding domain of the corresponding cell surface receptor. Such soluble receptors may be generated, for example, through mRNA that code for the soluble receptor or by enzymatic shedding of the ligand-binding extracellular domain of the cell surface receptor. The invention relates also to a number of related receptors termed "decoy receptors", which function to sequester secreted ligands. Examples of such decoy receptors are DcR1, DcR2, DcR3 and osteoprotegerin (OPG). Examples of binding proteins include, but are not limited to, cytokine binding proteins which do not correspond to a cell surface receptor, such as IL-18 binding protein (IL-18BP).

The circulatory system (scientifically known as the cardiovascular system) is an organ system that moves substances to and from cells; it can also help stabilize body temperature and pH (part of homeostasis) (wikipedia). The main components of the circulatory system are the heart, the blood, and the blood vessels.

The discovery that soluble forms of cytokine receptors and binding proteins are involved in the endogenous regulation of cytokine activity has prompted substantial interest in their potential application as immunotherapeutic agents. As such, soluble cytokine receptors have many advantages, including specificity, low immunogenicity and high affinity. The ability of many soluble cytokine receptors to inhibit the binding and biological activity of their ligands makes them very specific cytokine antagonists. In general, most agents based on soluble cytokine receptors have been safe, well-tolerated and have shown only minor side effects in the majority of patients. Soluble cytokine receptors constitute a new generation of therapeutic agents with tremendous potential for applications in a wide variety of human diseases (Idriss and Naismith 2000).

Soluble receptors or binding proteins of proinflammatory cytokines were proposed to neutralize and inhibit the action of such proinflammatory cytokines. Typically, such soluble receptors or binding proteins are administered in excess to neutralize the action of their respective proinflammatory cytokine. However, because of its large size, the resulting receptor/binding protein-cytokine complex may have a longer half-life in the circulation as compared with its individual constituents. Furthermore, the formation of the complex is reversible and hence the complex may serve as a long-acting source of the proinflammatory cytokine. Modification of the soluble receptors or binding proteins according to the present invention facilitates rapid clearance of the complex from the circulation without altering the binding capacity of the soluble receptor or binding protein to the proinflammatory cytokine. Thus, the invention provides a soluble receptor or binding protein to the pro-inflammatory cytokine, which is glycan-modified to carry a terminal Gal, GlcNAc or GalNAc to assist on the binding of the complex to specific receptors that are responsible or clearance of proteins from circulation such, as ASGP-R or any other lectin-type cell surface receptor. Therefore, administration of said glycan-modified soluble receptors or binding proteins is provided according to the invention to facilitate the rapid clearance of circulating proinflammatory cytokines. Similarly, soluble receptors or binding proteins of growth factors, which were modified to carry a terminal Gal, GlcNAc or GalNAc, are provided according to the invention. Administration of said soluble receptors or binding proteins of growth factors is provided according to the invention for effective and rapid clearance of undesired circulating growth factors, for example, growth factors which support tumor cell proliferation or vascular endothelial cell proliferation.

Another undesired component whose clearance from the circulation can be facilitated using the corresponding glycan-modified receptor or binding protein carrying a terminal Gal, GlcNAc or GalNAc is a lipoprotein or oxidized lipoprotein.

Thus in one aspect, the invention provides a glycan-modified receptor or binding protein carrying a terminal Gal, GlcNAc or GalNAc, and its use in the manufacture of a medicament for treating or preventing a disease or a disorder or condition whose pathogenesis or course is associated with the levels and/or activity of a component capable of binding said receptor or binding protein. Examples of said components include, but are not limited to, a cytokine, growth factor, lipoprotein and an oxidized lipoprotein.

In one embodiment, the invention provides a soluble receptor of the cytokine TNF-α, (p55), expressed in mammalian cells, whose N-glycan structure has been modified according to the invention. Such modified soluble TNF receptor (m-sTNFR) is useful, for example, for the treatment of diseases characterized by excess TNF, such as rheumatoid arthritis, Crohn's disease, psoriasis and various other autoimmune diseases. Administration of m-sTNFR to patients having said diseases leads to formation of a complex between the circulating TNF and the m-sTNFR. The resulting complex is rapidly cleared from the circulation by binding to ASGP-R or to any other lectin-type cell surface receptor. Following binding to the lectin-type receptor, the ternary complex consisting of the lectin-type receptor, m-sTNFR and TNF-α is internalized through a lectin receptor, the complex dissociates, m-sTNFR and TNF-α are degraded in the lysosome, whereas the lectin-type receptor recycles back to the cell surface.

Such lectin-type receptors are abundant in the liver, in macrophages, in vascular endothelial cells and in many other cell types.

Several general methods are known in the art for generating modified glycoproteins having terminal Gal, GlcNAc or GalNAc. These methods may be classified into three major groups: (1) Expression systems directed towards biosynthesis of glycoproteins with modified glycan structures; (2) Enzymatic transformations of glycoproteins and (3) chemical modifications of proteins. These methods can be employed for generating soluble cytokine receptors or binding proteins of the invention having terminal Gal, GlcNAc or GalNAc. In one embodiment of the invention, sTNFR p55, expressed in CHO cells, is treated with neuraminidase, which removes the terminal N acetyl neuraminic acid, thereby exposing the penultimate galactose residue. In another embodiment of the invention, said sTNFR is treated with neuraminidase followed by β-galactosidase to expose the GlcNAc residue. The resulting truncated glycoprotein may be used as such or even reacted with UDP-GalNAc in the presence of GalNAc transferase (βGalNAcT) (Rice, Thomas et al. 2003). Alternatively, sTNFR may be expressed in a system that incorporates GalNAc to the N-glycan moiety. For example, CHO-lec8 cells can be stably co-transfected with vectors expressing βGalNAcT and sTNFR p55. These cells will express and secrete sTNFR in which Gal residues are replaced by GalNAc. Treatment of the resulting glycoprotein with neuraminidase will expose the penultimate GalNAc (Kawar, Haslam et al. 2005). In another approach, sTNFR p55 can be treated with neuraminidase followed by β-galactosidase to remove the terminal N-acetyl neuraminic acid and the penultimate β-galactose. The resulting truncated glycoprotein can be then reacted with UDP-GalNAc in the presence of GalNAcT (Rice, Thomas et al. 2003). The resulting sTNFR with terminal GalNAc can be isolated on Wisteria Floribunda lectin-agarose column, which exhibits high specificity for glycoproteins terminating with GalNAc (Do, Do et al. 1997).

Alternatively, GalNAc may be added chemically to sTNFR expressed either in CHO cells or in a prokaryotic expression system such as E. coli. For example, it is possible to couple GalNAc or lactose directly to ε-amino groups of Lys residues in sTNFR by reductive amination with sodium cyanoborohydride. Similarly, two residues of GalNAc may be coupled to the ε and α amino groups of L-lysine and the resulting derivative is activated by water-soluble carbodiimide and then coupled to the ε-amino groups of Lys residues in sTNFR, thereby generating a spacer between the GalNAc residue and the sTNFR backbone. Other GalNAc synthons suitable for coupling to sTNFR were described in the literature. For example, compounds 5 and 8f of Westerlind et al (Westerlind, Westman et al. 2004) may be de-O-acetylated by mild alkali, activated by water-soluble carbodiimide and then coupled to sTNFR.

Since all cytokines and growth factors act through specific cell surface receptors, it is possible to express the extracellular domains of said receptors or binding proteins and then either modify their N- or O-glycans as described for the N-glycans of sTNFR p55. Alternatively, desired saccharide residues may be added chemically to such soluble receptors or binding proteins. The following list of cytokines and growth factors are examples of effector molecules that can be rapidly and efficiently cleared from the circulation using the corresponding soluble receptor or binding protein whose glycan moiety was modified according to the invention employing one or more of the methods described above for sTNFR p55: IL-1α, IL-1β, IL-2, IL-3, IL-4/IL-13, IL-5, IL-7, IL-9, IL-10, IL-12, IL-14, IL-15, IL-17, IL-18, IL-19, IL-20, IL-21, IL-22, IL-23, IL-24, IL-25, IL-26, IL-28A, IL-28B, IL-29, activin, apo2L/TRAIL, APRIL, BAFF, TNFSF9, BMP-2, CD27L, BMP-3, BMP-7, CD30L, CD40L, CNTF, EGF, VEGF, FASL, FGF, CSF, FLT3, G-CSF, GDNF, GITRL, GM-CSF, GH, HGF, IGF I & II, IFN-α, IFN-γ, LIGHT, lymphotoxin, M-CSF, MSP, NGF, NT-3, NT-4, OX-40L, PDGF, Prolactin, SCF, TGF-α, TGF-β, TPO, TRANCE, TSLP, TWEAK.

Tools known in the art for molecular, biochemical, microbiological and recombinant DNA techniques can be found in the following literature: Selected Methods in Cellular Immunology, W.H. Freeman and Co., New York (1980); Oligonucleotide Synthesis Gait, M. J., ed. (1984); Transcription and Translation Hames, B. D., and Higgins S. J., Eds. (1984); Animal Cell Culture Freshney, R. I., ed. (1986); Immobilized Cells and Enzymes IRL Press, (1986); Nucleic Acid Hybridization Hames, B. D., and Higgins S. J., eds. (1985); A Practical Guide to Molecular Cloning, John Wiley & Sons, New York (1988); Molecular Cloning: A laboratory Manual Sambrook et al., (1989); Academic Press; PCR Protocols: A Guide To Methods And Applications, Academic Press, San Diego, Calif. (1990); Perbal, Watson et al., Recombinant DNA, Scientific American Books, New York; Birren et al. (eds) Genome Analysis: A Laboratory Handbook, Cellis, J. E., ed. (1994); Current Protocols in Immunology Coligan J. E., ed. (1994); Stites et al. (eds), Basic and Clinical Immunology, Appleton & Lange, Norwalk, Conn. (1994); Mishell and Shiigi (eds); Marshak et al., Strategies for Protein Purification and Characterization—A Laboratory Course Manual CSHL Press (1996); and A Laboratory Manual Series, Cold Spring Harbor Laboratory Press, New York (1998); Methods in Enzymology Vol. 1-317.

Because the ASGP-R is highly abundant on hepatocytes, which carry 150,000-500,000 binding sites/cell and because additional lectin receptors are also present on many cell types, the clearance of complexes consisting of cytokines or growth factors with their respective soluble receptor that carries exposed Gal, GlcNAc or GalNAc will be very rapid. Information available just for one of this lectin-type receptor, the ASGP-R, demonstrates the efficacy of the clearance. Thus, the number of hepatocytes present in the liver is about $2 \times 10^8$ per mouse and the rate of ASGP-R internalization is 0.1 pmol/min per $10^6$ cells. On the basis of such estimates, the mouse liver is capable of removing about 1.2 nmol/h of ligand through the ASGP-R, or the equivalent of 2.4 µg/h of a glycoprotein with a molecular weight of 20,000 (Park, Mi et al. 2005). Extrapolation to a human liver suggests an almost unlimited potential clearance rate of over 5 mg/h or 120 mg/day of e.g., TNF-α complexed with m-sTNFR.

Figure 2:
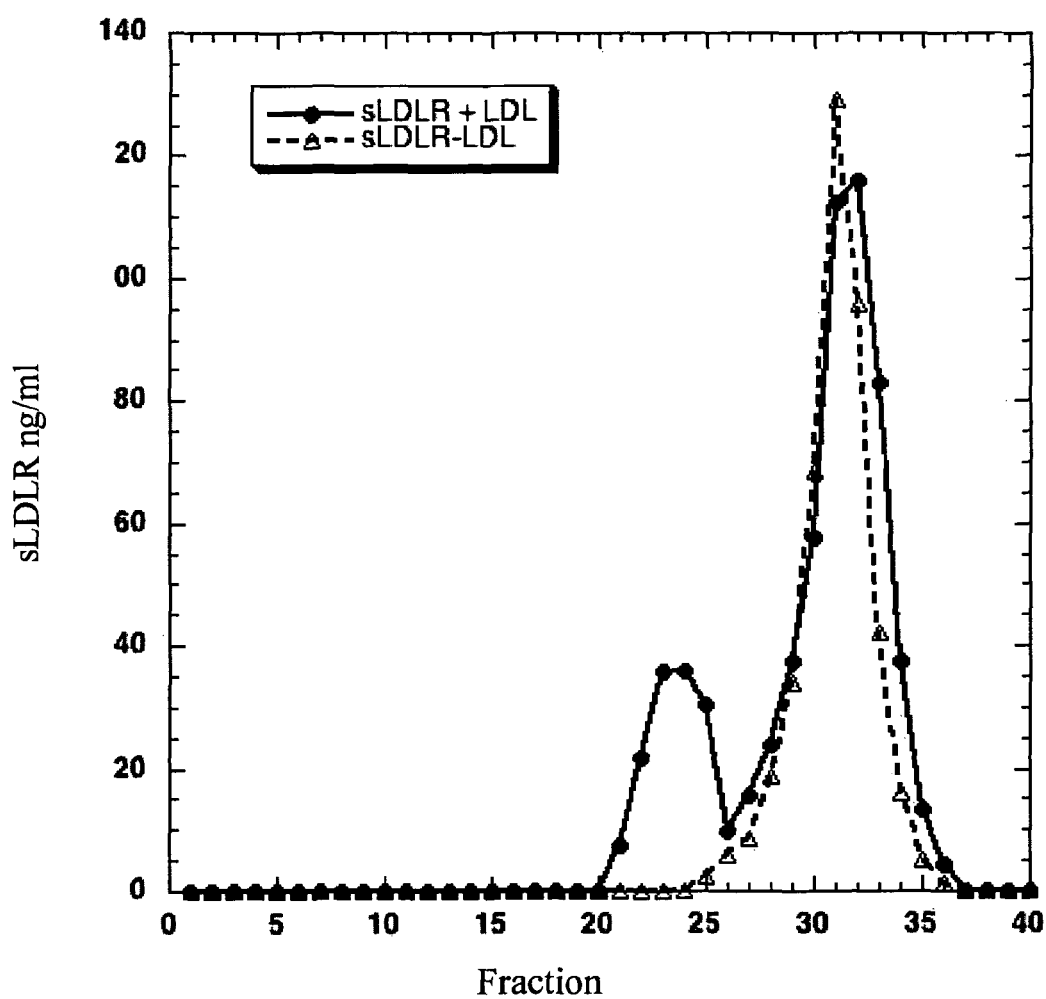
FIG. 2 shows results of sLDLR ELISA of fractions obtained by size exclusion chromatography of sLDLR on a Superose 6 column in the presence (solid line) or absence (dashed line) of LDL.

We have isolated a soluble protein corresponding to the ligand-binding domain of the human LDLR (sLDLR) by virtue of its antiviral activity against vesicular stomatitis virus (Fischer, Tal et al. 1993). We then characterized a recombinant sLDLR that was expressed in Chinese hamster ovary (CHO) cells (amino acid residues 25-352 of the LDLR precursor; accession No. P01130, SwissProt/ExPASy database). Unexpectedly, it was found according to the invention that this soluble LDLR (sLDLR) is N-glycosylated, as determined by SDS-PAGE before and after cleavage with PNGase (FIG. 1). The N-glycosylation site was found to be on Asn 272 of the LDLR precursor by comparing the mass-spectrometric profile of tryptic peptide digests before and after treatment with PNGase (Table 1). It was found according to the invention that N-glycosylated sLDLR binds to LDL and that the binding resists dissociation at physiological conditions, as determined by size exclusion chromatography in phosphate buffered saline pH 7.4 (FIG. 2). Thus, sLDLR, which carries a terminal GalNAc (sLDLR-Gn), is provided according to the invention. sLDLR-Gn according to the invention can include, for example, a polypeptide of LDLR precursor spanning amino acid residues 25 to 352 containing seven imperfect repeats which comprise the entire LDL binding site as well as repeat A of the EGF-precursor-homologous domain (reported to contribute to ligand binding); and a polypeptide of LDLR precursor spanning amino acid residues 25 to 313 containing seven imperfect repeats which comprise the entire LDL binding site. Administration of sLDLR-Gn is provided according to the invention for facilitating effective and rapid reduction of cholesterol in the circulation. Such administration is beneficial for individuals with familial hypercholesterolemia due to mutated LDLR or reduced LDLR, as well as to other persons whose LDLR level or LDLR function is reduced. Administration of sLDLR-Gn is also beneficial for individuals who do not tolerate other means of reducing serum cholesterol such as HMG-CoA inhibitors. Administration of sLDLR-Gn is of particular value to patients such as certain familial hypercholesterolemia patients who cannot manage their serum cholesterol by any of the existing methods and therefore depend on LDL apheresis.

Several general methods known in the art can be utilized for generating sLDLR or its related homologous having terminal GalNAc. In one embodiment of the invention, CHO-lec8 cells can be stably co-transfected with vectors expressing β-GalNAc Transferase (βGalNAcT) and sLDLR. These cells will express and secrete sLDLR-Gn, which may be treated with neuraminidase to expose the penultimate GalNAc (Kawar, Haslam et al. 2005). In another approach, sLDLR can be expressed in a host cell such as CHO cell and collected from the culture supernatant. The sLDLR produced can be treated with neuraminidase followed by β-galactosidase to remove the terminal N-acetyl neuraminic acid and the penultimate β-galactose. The resulting truncated glycoprotein can be then reacted with UDP-GalNAc in the presence of GalNAcT (Rice, Thomas et al. 2003). The resulting sLDLR-Gn can be isolated on Wisteria Floribunda lectin-agarose column, which exhibits high specificity for glycoproteins terminating with GalNAc (Do, Do et al. 1997).

Alternatively, GalNAc can be added chemically to sLDLR or to its related homologous. For example, it is possible to couple N-acetyl galactosamine (GalNAc) directly to ε-amino groups of Lys residues in sLDLR by reductive amination with sodium cyanoborohydride. Similarly, two residues of GalNAc can be coupled to the c and a amino groups of L-lysine and the resulting derivative can be activated by water-soluble carbodiimide and then coupled to the ε-amino groups of Lys residues in sLDLR, thereby generating a spacer between the GalNAc residue and the sLDLR backbone. Other GalNAc synthons suitable for coupling to sLDLR were described in the literature. For example, compounds 5 and 8f of Westerlind et al (Westerlind, Westman et al. 2004) are de-O-acetylated by mild alkali, activated by water-soluble carbodiimide and then coupled to sLDLR.

The rate of synthesis and catabolism of apoB is 8.0±0.7 mg/kg/day in normal individuals, 13.8±3.6 mg/kg/day in FH heterozygotes and 26.4±10 mg/kg/day in FH homozygotes (Bilheimer, Stone et al. 1979). Thus, the catabolic rate is normalized in FH heterozygotes by eliminating 5.8±3.6 mg/kg/day of plasma apoB. Since the molecular mass of glycosylated sLDLR is 34,000 and that of apoB is 550,000 (Johs, Hammel et al. 2006), administration of at least 0.36±0.22 mg/kg/day of a sLDLR-Gn derivative normalizes the catabolic rate of LDLR in FH heterozygotes, assuming 100% efficiency. However, the resulting enhanced uptake of cholesterol by hepatocytes further down-regulates the expression of the cell surface LDLR, requiring dose escalation. At the extreme case, a dose of 0.85±0.5 mg/kg/day of a sLDLR-Gn derivative will internalize the entire cholesterol output of heFH patients. Binding of sLDLR to apoE-containing lipoproteins is also taking place. Since apoE is present in both the very large VLDR and the much smaller HDL-ApoE, the precise effect of apoE presence in lipoproteins cannot be evaluated and optimal dose of sLDLR-Gn will have to be determined experimentally.

Two or more structures are said to be homologous if they are alike because of shared ancestry. Homology among proteins and DNA is often concluded on the basis of sequence similarity, especially in bioinformatics. For example, in general, if two genes have an almost identical DNA sequence, it is likely that they are homologous. Many algorithms exist to cluster protein sequences into sequence families, which are sets of mutually homologous sequences. Homology of sequences can be of two types: orthologous or paralogous. Two similar genes in two different species that originated from a common ancestor are orthologous. Homologous sequences are orthologous if they were separated by a speciation event: if a gene exists in a species, and that species diverges into two species, then the divergent copies of this gene in the resulting species are orthologous. A second definition of orthologous describes any two genes in two different species with very similar functions. Homologous sequences are paralogous if they were separated by a gene duplication event: if a gene in an organism is duplicated to occupy two different positions in the same genome, then the two copies are paralogous. The genes encoding myoglobin and hemoglobin are considered to be ancient paralogs.

Similar methods are provided according to the invention for expressing soluble scavenger receptors corresponding to the extracellular ligand-binding domains of their respective cell-associated receptors and carrying GalNAc instead of Gal. Such modified soluble receptors bind oxidized lipoproteins such as oxLDL and oxRLP, ferry them to the liver, where the complex rapidly binds to ASGP-R, is internalized and degraded. As in the case of sLDLR, recombinant soluble scavenger receptors can be expressed in host cells such as CHO-lec8 cells, and stably co-transfected with vectors expressing βGalNAcT. The soluble scavenger receptor constructs have the general layout that includes a sequence coding for a signal peptide followed by a DNA coding for any one of the extracellular domain of said scavenger receptors. The secreted product can be treated with neuraminidase to expose the penultimate GalNAc (Kawar, Haslam et al. 2005). In another approach, any one of the soluble scavenger receptors can be expressed in a host cell such as CHO cells and isolated from the culture medium. After isolation, the soluble receptor can be treated with neuraminidase followed by β-galactosidase to remove the terminal N-acetyl neuraminic acid and the penultimate β-galactosidase. The resulting truncated glycoprotein can be reacted with UDP-GalNAc in the presence of GalNAcT (Rice, Thomas et al. 2003). The resulting modified soluble scavenger receptor can be isolated on Wisteria Floribunda lectin-agarose column, which exhibits high specificity for glycoproteins terminating with GalNAc (Do, Do et al. 1997).

Alternatively, GalNAc can be added chemically to a soluble scavenger receptor. For example, N-acetyl galactosamine (GalNAc) can be directly coupled directly to ε-amino groups of Lys residues in said soluble scavenger receptor by reductive amination with sodium cyanoborohydride. Similarly, two residues of GalNAc can be coupled to the E and a amino groups of L-lysine and the resulting derivative is activated by water-soluble carbodiimide and then coupled to the ε-amino groups of Lys residues in any one of the soluble scavenger receptors, thereby generating a spacer between the GalNAc residue and said receptor backbone. Other GalNAc synthons suitable for coupling to various proteins were described in the literature. For example, compounds 5 and 8f of Westerlind et al (Westerlind, Westman et al. 2004) are de-O-acetylated by mild alkali, activated by water-soluble carbodiimide and then coupled to any one of the soluble scavenger receptors.

The present invention encompasses pharmaceutical compositions comprising an active substance comprising a glycan-modified soluble receptor or binding protein according to the invention.

The therapeutically effective amounts of the active protein(s) will be a function of many variables, e.g. the route of administration, the clinical condition of the patient.

A "therapeutically effective amount" is such that when administered, the glycan-modified soluble receptor or binding protein, exhibit biological activity. The dosage administered, as single or multiple doses, to an individual will vary depending upon a variety of factors, including pharmacokinetic properties, the route of administration, patient conditions and characteristics (sex, age, body weight, health, and size), extent of symptoms, concurrent treatments, frequency of treatment and the effect desired. Adjustment and manipulation of established dosage ranges are well within the ability of those skilled in the art, as well as in vitro and in vivo methods of determining the effect in an individual.

All the information contained in the references provided is incorporated herein by reference.

The invention will now be illustrated by the following non-limiting examples:

EXAMPLES

Example 1

Generation of asialo sTNFR p55

Neuraminidase (New England Biolabs, Cat. No. P0720L) 50,000 units in 1 ml PBS is immobilized on Affigel 10 (1 ml packed beads, BioRad Labs) according to the manufacturer's instructions and packed into a column. Recombinant sTNFR p55 corresponding to amino acids 22-211 of pro-TNF-R1 (www.expasy.org/uniprot/P19438), expressed in CHO cells (1 g, Merck Serono laboratories) in citrate buffer (50 mM, pH 6, 10 ml) is circulated through the immobilized neuraminidase column for 2 h at 25° C. The resulting asialo sTNFR (as-sTNFR) is collected and dialyzed against PBS (500 ml, three changes) to remove free N-acetyl neuraminic acid.

Example 2

Removal of β1-3 galactose from asialo sTNFR p55

β1-3 galactosidase (New England Biolabs, Cat. No. P0726L) 10,000 units in 1 ml PBS is immobilized on Affigel 10 (1 ml packed beads, BioRad Labs) according to the manufacturer's instructions and packed into a column. Asialo-sTNFR p55, produced as described in Example 1 (1 g) in acetate buffer (50 mM, pH 4.5, 10 ml) is circulated through the immobilized β-galactosidase column for 2 h at 25° C. The resulting asialo, agalacto sTNFR (as-ag-sTNFR) is collected and dialyzed against PBS (500 ml, three changes) to remove free galactose.

Example 3

Lactosamination of sTNFR p55

Lactose (270 mg, 0.79 mmol, Sigma) is added to recombinant sTNFR p55, corresponding to amino acids 22-211 of pro-TNF-R1 (www.expasy.org/uniprot/P19438) expressed in *E. coli* (1 g, PeproTech Inc.) in NaHCO3 (50 mM, 10 ml, pH 8.4), followed by addition of sodium cyanoborohydride (48 mg, 0.79 mmol). The solution is kept for 170 h at room temperature. The lactosaminated sTNFR (lac-sTNFR) is dialyzed against PBS (500 ml, three changes) to remove the low molecular weight components.

Example 4

Expression of Recombinant sTNFR p55 with Terminal GalNAc

CHO Lec8 cells (ATCC CRL-1737) were transfected as described (Kawar, Haslam et al. 2005) with a plasmid encoding the complete open reading frame of Ceβ4GalNAcT under the control of the CMV promoter; this plasmid also encoded a Geneticin resistance gene. The cells were cultured in Dulbecco's modified Eagle's medium, containing 10% fetal calf serum and 600 µg/ml Geneticin (invitrogen), to select for stably transformed cells. After 4 weeks in culture, a cell line expressing the Ceβ4GalNAcT activity (L8-GalNAcT was cloned from a single cell by limiting-dilution culturing as described (Kawar, Haslam et al. 2005).

L8-GalNAcT cells are then transfected, as above, with a mammalian expression plasmid pCDNA4/His (Invitrogen) encoding the open reading frame of human TNFR (p55) from codon 1 to 211 including the cognate signal peptide for secretion (www.expasy.org/uniprot/P19438), followed by a stop codon under the control of the CMV promoter; this plasmid also encodes a zeocin resistance gene. The cells are then cultured in Dulbecco's modified Eagle's medium containing 10% fetal calf serum, 600 µg/ml Geneticin, and 400 µg/ml zeocin (Invitrogen) to select for stably transformed cells. After 4 weeks in culture, a cell line expressing GalNAcT and sTNFR is cloned from a single cell as described (Selmaj 2000; Kawar, Haslam et al. 2005).

Example 5

Recombinant sLDLR Expressed in CHO Cells is a Glycoprotein

Cummings et al found that the human LDLR contains a single Asn-linked oligosaccharide (Cummings, Kornfeld et al. 1983) (see paragraph 3 in p. 15269, right column). The N-glycosylation site was located at Asn 657 of pro-LDLR (www.expasy.org/uniprot/P01130). All O-glycosylation sites are clustered at an exrtacellular domain adjacent to the plasma membrane (Gent and Braakman 2004). Therefore, the sLDLR 25-352 is not expected to be glycosylated. sLDLR of 328 amino acid residues (corresponding to amino acid residues Asp25 to Cys352 of pro sLDLR) was produced in CHO cells (InterPharm laboratories, Ness Ziona, Israel). Briefly, the expression plasmid constructed for transfection of DHFR-deficient CHO cells, contained both the DNA sequence encoding the polypeptide spanning amino acid residues 1-352 of pro hsLDLR [(including a cognate 24 amino acid signal peptide and the following 328 amino acid residues of the mature polypeptide (spanning amino acids 25-352 of the LDLR precursor protein)] and the murine DHFR on the same plasmid, when both hsLDLR and DHFR expression was controlled by a promoter and transcription termination elements from SV40.

The DNA fragment encoding 1-352 amino acid residues of pro hsLDLR was isolated by PCR amplification using the entire pro LDLR gene as template (cDNA of LDLR, Yamamoto et al. Cell 39: 27-38, 1984). Amplification was carried out employing PCR reaction mixtures containing 1 ng of template, 400 ng of each primer (forward and reverse), 0.2 nM dNTP mix, 2 mM MgCl$_2$, 5 U Pfu DNA polymerase, in the buffer supplied with the enzyme, in a total volume of 100 microliter. 31 thermal cycles were employed (1 min 94° C., 1 min 65° C., 2 min 72° C.), preceded by 2 min heating at 94° C. and followed by 10 mM at 72° C. The primers used were the forward primer (SEQ ID NO: 1) 5' CCC AAGCTT CCACC ATG GGG CCC TGG GGC TG including the Hind III site, the Kozak sequence and the sequence encoding the first 5 amino acids of the pro hsLDLR and the reverse primer (SEQ ID NO: 2) 5' CCG GGATCC TTA CTA GCA TCT TCG CTG GGC CAC C including the BamHI site, two stop codons and the sequence of the last 6 amino acids, the last one being Cys 352. An intermediate plasmid including the expression cassette of hsLDLR was obtained by digesting the PCR product with Hind III and Bam HI and introducing it to the pSVE3 plasmid previously digested with HINDIII and BclI (digestion with these enzymes remove most of the SV40 early region of the pSVE3). A final plasmid including the expression cassettes of hsLDLR and DHFR was obtained by digesting the intermediate plasmid with BamHI, isolating the hsLDLR expression cassette, and ligating it to the large fragment of pDHFR previously digested with BamHI. After verification of the final construct by restriction map and sequence analysis, by methods known in the art, cells were transfected with the final plasmid and subjected to selective medium in order to select for DHFR positive cells. Transfection was carried out by cationic liposomes using LipofectAmine (Gibco BRL), according to the protocol described by the manufacturer. Seventy-two hours after transfection cells were transferred to a selective medium lacking deoxy and ribonucleosides and supplemented with 10% dialysed FCS. Cells expressing DHFR activity were able to form colonies in the selective medium, which were isolated by lifting the cells with trypsin-soaked paper discs. The isolated cells were grown and screened for r-hsLDLR antiviral activity, essentially as described in example 9 of U.S. Pat. No. 6,849,720. The transfected cells producing r-hsLDLR were then subjected to gene amplification by gradually increasing MTX concentration, followed by subcloning and selection of stable producer clones. r-hsLDLR was produced from the medium of such a stable CHO producer clone, essentially as indicated in Example 1 of U.S. Pat. No. 6,849,720 describing the production of a shorter version of hsLDLR lacking Cys 313 (spanning amino acids 25-312 from pro sLDLR, referred in the patent as the 291 form) and therefore containing an odd number of Cys residues.

The r-hsLDLR produced was digested with PNGase (15,000 Units, New England Biolabs, Cat. No. P0704S), according to the manufacturer's instructions. Aliquot of undigested and digested sLDLR (1 µg each) were resolved on a gradient polyacrylamide gel (8-15% acrylamide) and then stained with coomassie blue. A significant increase in mobility of r-hsLDLR was seen following digestion, indicating that r-hsLDLR 25-352 expressed in CHO cells is a glycoprotein (FIG. 1).

Example 6

Determination of the Glycosylation Point in sLDLR

The bands corresponding to non-treated and PNGase-digested r-hsLDLR of Example 5 were excised from the gel, reduced and alkylated and then digested with trypsin. The resulting peptide mixtures were subjected to MALDI-TOF mass spectrometry. Comparison of the peptides identified in the two preparations revealed one new peptide (peptide 17) that emerged following PNGase (Table 1). This peptide corresponds to the peptide DMSDEVGCVNVTLCEGPNK (SEQ ID NO: 3), which contains a potential N-glycosylation site at Asn 272 of proLDLR.

TABLE 1

Tryptic peptides identified by MALDI-TOF MS from sLDLR before and after deglycosylation with PNGase.

| Peptide No. | Resulting Peptide | SEQ ID NO | Length | Control | PNGase |
|---|---|---|---|---|---|
| 1 | CERNEFQCQDGKCISYK | 4 | 12 | √ | |
| 2 | NEFQCQDGK | 5 | 9 | | √ |
| 3 | NEFQCQDGKCISYK | 6 | 14 | √ | |
| 4 | CISYK | 7 | 5 | √ | √ |
| 5 | SGDFSCGGR | 8 | 9 | √ | √ |
| 6 | SGDFSCGGRVNR | 9 | 12 | √ | |
| 7 | CIPQFWR | 10 | 7 | √ | √ |
| 8 | VNRCIPQFWR | 11 | 10 | | √ |
| 9 | TCSQDEFR | 12 | 8 | √ | √ |
| 10 | CHDGK | 13 | 5 | √ | |
| 11 | CHDGKCISR | 14 | 9 | √ | √ |
| 12 | QFVCDSDR | 15 | 8 | √ | |
| 13 | CDGGPDCK | 16 | 8 | | √ |
| 14 | DKSDEENCAVATCR | 17 | 14 | √ | |
| 15 | QCDREYDCK | 18 | 9 | √ | |
| 16 | EYDCK | 19 | 5 | √ | |
| 17 | DMSDEVGCVNVTLCEGPNK | 3 | 19 | | √ |
| 18 | CHSGECITLDK | 20 | 11 | √ | √ |
| 19 | VCNMAR | 21 | 6 | √ | |
| 20 | VCNMARDCR | 22 | 9 | √ | √ |
| 21 | DWSDEPIK | 23 | 8 | √ | √ |

Example 7

Recombinant sLDLR Binds LDL

Attempts to demonstrate the binding of recombinant sLDLR produced in CHO cells to LDL by surface plasmon resonance (BIAcore) were unsuccessful. Therefore, we employed another method for testing the binding of sLDLR to LDL. For this purpose, we incubated for 1 h at 37° C. a solution of LDL (Biomedical technologies, Inc, Ma, USA) and r-hsLDLR of Example 5 at a final concentration of 7 micromolar each in PBS plus 10 micromolar Calcium Chloride (PBS+). An aliquot of 0.1 ml was subjected to size exclusion chromatography on a Superose 6 HR 10/30 column (GE Healthcare Life Sciences Cat. No 17-5172-01). The column was eluted with PBS+ at a flow rate of 0.4 ml/min and fractions of 0.5 ml were collected. The concentration of r-hsLDLR was determined by a specific ELISA as follows: Mab #28 anti-human sLDLR (5 microgram/ml in PBS; corresponding to Mab from hybridoma clone 28 deposited at the CNCM under No. 1-2391-U.S. Pat. No. 6,849,720) was used for coating of 96-well ELISA plates at 0.1 ml/well overnight at room temperature. The plates were then washed ×3 with PBS containing 0.05% Tween-20 and then blocked by 0.3 ml blocking buffer (1% bovine serum albumin, 5% sucrose, 0.05% sodium azide in PBS). The plates were then washed 3× with PBS. Standard recombinant sLDLR 25-352 expressed in CHO cells (125 ng/ml, InterPharm Laboratories, Ness Ziona, Israel) in 0.1 ml PBS was added to a first well and diluted twofold serially. Samples containing unknown amounts of sLDLR were added to the first well of other rows and diluted twofold serially as well. The plates were then incubated 2 h at room temperature and then washed 3× with the blocking buffer. Biotinylated mab #29.8 anti-human sLDLR (corresponding to Mab from hybridoma clone 29.8 deposited at the CNCM under No. 1-2392-U.S. Pat. No. 6,849,720), diluted to 4 microgram/ml in reagent diluent (1% bovine serum albumin in PBS, 0.1 ml) was added to each well and incubated 2 h at room temperature. The plates were then washed 3× with reagent diluent. Streptavidin HRP(R&D systems) in reagent diluent at a working dilution (0.1 ml) was added to each well according to the manufacturer (R&D Systems) instructions and the plates were incubated 20 min at room temperature. The plated were then washed 3× with reagent diluent, a substrate solution (0.1 ml TMB/E, Chemicon) is added to each well and the plates were either read within 5 min at 630 nm or stopped with $H_2SO_4$ (2 N 0.05 ml) and read at 450 nm. Optical imperfections of the plate were corrected by subtracting the reading at 540 nm or 570 nm.

Chromatography of sLDLR alone (FIG. 2 dashed line) revealed a peak of free sLDLR eluting in fractions 27-35, peaking in fraction 31. Chromatography of the LDL-sLDLR complex revealed a peak of sLDLR eluting at a higher molecular mass in fractions 20-26, identical to that of LDL (avg. mass $2.5 \times 10^6$ Da) migration as well as a large peak of free sLDLR. Based on the ratio of the two peaks as determined by ELISA of sLDLR and assuming a dilution of 5 fold over the initial concentration we estimate a KD of the LDL-sLDLR complex in the 10 nanomolar range.

Example 8

N-acetylgalactosamination of sLDLR Expressed in *E. Coli*

Recombinant sLDLR (amino acids 25-352 of the proLDLR, www.expasy.org/uniprot/P01130) is expressed in *E. coli*, refolded and purified essentially as described (Simmons, Newhouse et al. 1997). N-acetyl galactosamine (100 mg, 0.46 mmol. Calbiochem) is added to 1 g of sLDLR25-352 in NaHCO3 buffer (50 mM, pH 8.4, 10 ml), followed by addition of sodium cyanoborohydride (Sigma, 28 mg, 0.46 mmol). The solution is kept for 170 h at room temperature. The N-acetyl galactosaminated sLDLR25-352 (sLDLR-Gn) is dialyzed against PBS (500 ml, three changes) to remove the low molecular weight components.

Example 9

N-acetylgalactosamination of a sLDLR Fragment in *E. Coli*

A recombinant sLDLR fragment capable of selectively binding apoE-containing lipoproteins (amino acids 146-233 of the proLDLR, www.expasy.org/uniprot/P01130) is expressed in *E. coli*, refolded and purified essentially as described (Fisher, Abdul-Aziz et al. 2004). N-acetyl galactosamine (340 mg, 1.5 mmol) is added to 1 g of sLDLR146-233 in NaHCO3 (50 mM, pH 8.4, 10 ml), followed by addition of sodium cyanoborohydride (91 mg, 1.5 mmol). The solution is kept for 170 h at room temperature. The N-acetyl galactosaminated sLDLR146-233 is dialyzed against PBS (500 ml, three changes) to remove the low molecular weight components.

Example 10

Expression of sLDLR with Terminal GalNAc

L8-GalNAcT cells of Example 4 were transfected, as above, with a plasmid pCDNA4/His (Invitrogen), encoding the open reading frame of human LDLR from codon 1 to 315, including the cognate signal peptide for secretion www.expasy.org/uniprot/P01130). followed by a stop codon, under the control of the CMV promoter; this plasmid also encoded a zeocin resistance gene. The cells were then cultured in Dulbecco's modified Eagle's medium containing 10% fetal calf serum, 600 µg/ml Geneticin, and 400 µg/ml zeocin to select for stably transformed cells. After 4 weeks in culture, a cell line expressing GalNAcT as determined by RT-PCR and sLDLR as determined by ELISA described in Example 7 was cloned from a single cell as above. sLDLR having a penultimate GalNAc instead of Gal in its N-glycan (sLDLR-Gn) is isolated from culture supernatants of these CHO cells and purified using chromatographic methods known in the art. sLDLR-Gn is treated with immobilized neuraminidase to remove the terminal N-acetyl neuraminic acid residues. The sLDLR-Gn is dialyzed against PBS (500 ml, three changes) to remove the low molecular weight components.

Example 11

N-acetylgalactosamination of a Soluble oxLDL Receptor Fragment Expressed in E. Coli A recombinant fragment of OLR1/LOX-1 capable of selectively binding oxLDL (amino acids 143-273 of OLR1/LOX-1) is expressed in E. coli, refolded and purified essentially as described (Smirnova, Sawamura et al. 2004) (Ishigaki, Ohki et al. 2005). N-acetyl galactosamine (340 mg, 1.5 mmol) is added to 1 g of sOLR1/LOX-1143-273 in NaHCO3 (50 mM, pH 8.4, 10 ml), followed by sodium cyanoborohydride (91 mg, 1.5 mmol). The solution is kept for 170 h at room temperature. The N-acetyl galactosaminated sOLR1/LOX 1143 273 (sOLR1/LOX-1-Gn) is dialyzed against PBS (500 ml, three changes) to remove the low molecular weight components.

Example 12

Expression of sOLR1/LOX-1 with Terminal GalNAc

L8-GalNAcT cells of Example 4 are transfected, as above, with plasmid pCDNA4/His (Invitrogen) encoding the signal peptide followed by codons 58-273 of the open reading frame of human OLR1/LOX-1 (www.expasy.org/uniprot/P78380), followed by a stop codon, under the control of the CMV promoter. This plasmid also encoded a zeocin resistance gene. The cells are then cultured in Dulbecco's modified Eagle's medium containing 10% fetal calf serum, 600 µg/ml Geneticin, and 400 µg/ml zeocin to select for stably transformed cells. After 4 weeks in culture, a cell line expressing GalNAcT and sOLR1/LOX-1 is cloned from a single cell as above. sOLR1/LOX-1 having a penultimate GalNAc instead of Gal in its N-glycans (sOLR1/LOX-1-Gn) is isolated from culture supernatants of these CHO cells and purified with chromatographic methods well known in the art. sLDLR-Gn is treated with immobilized neuraminidase to remove the terminal N-acetyl neuraminic acid residues. The N-acetyl galactosaminated sOLR1/LOX-1 (sOLR1/LOX-1-Gn) is dialyzed against PBS (500 ml, three changes) to remove the low molecular weight components.

Example 13

Expression of sVEGF Receptor 2 with Terminal Galactose

A soluble form of the VEGF receptor 2 (sFlk-1) from amino acid 20 to 764 (www.expasy.org/uniprot/P35968) is expressed in a baculovirus system essentially as described (Huang, Gottstein et al. 1998). The resulting sFlk-1 is purified employing chromatographic methods well known in the art and treated with PNGase (15,000 Units, New England Biolabs, Cat. No. P0704S), immobilized on Affigel 10 (1 ml packed beads BioRad Labs), according to the manufacturer's instructions, followed by chemical lactosamination, as described in Example 3, to yield lactosaminated sFlk-1 (lac-sFLK-1). The lac-sFLK-1 is dialyzed against PBS (500 ml, three changes) to remove the low molecular weight components.

Example 14

Removal of Excess TNF-Alpha from the Circulation of Rats

Human TNF-alpha in PBS (1 mg/ml, in 0.1 ml PBS) is injected into the tail vein of anesthetized adult rat (300 g), either with PBS (0.1 ml), with sTNFR p55 (5 mg/ml in 0.1 ml PBS) or with asialo sTNFR p55 of Example 1 (5 mg/ml in 0.1 ml PBS). Starting at time 0, blood samples (0.1 ml) are withdrawn at 20 min intervals for 120 min. Serum is collected and the level of serum TNF is determined by ELISA. The half life of serum TNF is 30 min. It is increased upon co-administration of sTNFR p55 and decreased upon co-administration of asialo-sTNFR p55.

Example 15

Treatment of Rheumatoid Arthritis with Asialo TNFR

As-sTNFR of Example 1 is administered to a rheumatoid arthritis patient subcutaneously at a daily dose of 50 mg/sq. m.

Example 16

Treatment of Familial Hypercholesterolemia with sLDLR-Gn sLDLR-Gn of Example 8 or 10 is administered to a patient whose serum cholesterol is above 200 mg % subcutaneously or by infusion at a daily dose of 50 mg/sq. m.

Example 17

Treatment of Patients with High Risk of Developing Atherosclerosis with sOLR1/LOX-1-Gn sOLR1/LOX-1-Gn of Example 11 or 12 is administered to a patient whose serum cholesterol is above 200 mg % subcutaneously at a daily dose of 50 mg/sq. m.

Example 18

Treatment of Cancer Patients with lac-sFLk-1 lac-sFLK-1 of Example 13 is administered to a cancer patient subcutaneously at a daily dose of 50 mg/sq. m.

REFERENCES

Bernini, F., S. R. Tanenbaum, et al. (1986). "Enhanced catabolism of low density lipoproteins in rat by lactosaminated Fab fragment. A new carrier of macromolecules to the liver." *J Biol Chem* 261(20): 9294-9.

Bilheimer, D. W., N. J. Stone, et al. (1979). "Metabolic studies in familial hypercholesterolemia. Evidence for a gene-dosage effect in vivo." *J Clin Invest* 64(2): 524-33.

Brown, M. S. and J. L. Goldstein (1986). "A receptor-mediated pathway for cholesterol homeostasis." *Science* 232 (4746): 34-47.

Cardona, F., F. J. Tinahones, et al. (2003). "The elevated prevalence of apolipoprotein E2 in patients with gout is associated with reduced renal excretion of urates." *Rheumatology (Oxford)* 42(3): 468-72.

Civeira, F. (2004). "Guidelines for the diagnosis and management of heterozygous familial hypercholesterolemia." *Atherosclerosis* 173(1): 55-68.

Cummings, R. D., S. Kornfeld, et al. (1983). "Biosynthesis of N- and O-linked oligosaccharides of the low density lipoprotein receptor." *J Biol Chem* 258(24): 15261-73.

Do, K. Y., S. I. Do, et al. (1997). "Differential expression of LacdiNAc sequences (GalNAc beta 1-4GlcNAc-R) in glycoproteins synthesized by Chinese hamster ovary and human 293 cells." *Glycobiology* 7(2): 183-94.

Fischer, D. G., N. Tal, et al. (1993). "An antiviral soluble form of the LDL receptor induced by interferon." *Science* 262 (5131): 250-3.

Fisher, C., D. Abdul-Aziz, et al. (2004). "A two-module region of the low-density lipoprotein receptor sufficient for formation of complexes with apolipoprotein E ligands." *Biochemistry* 43(4): 1037-44.

Gent, J. and I. Braakman (2004). "Low-density lipoprotein receptor structure and folding." *Cell Mol Life Sci* 61(19-20): 2461-70.

Goldsmith, D. R. and A. J. Wagstaff (2005). "Spotlight on etanercept in plaque psoriasis and psoriatic arthritis." *BioDrugs* 19(6): 401-3.

Grundy, S. M. (1983). "Absorption and metabolism of dietary cholesterol." *Annu Rev Nutr* 3: 71-96.

Hatters, D. M., C. A. Peters-Libeu, et al. (2006). "Apolipoprotein E structure: insights into function." *Trends Biochem Sci* 31(8): 445-54.

Heaney, M. L. and D. W. Golde (1998). "Soluble receptors in human disease." *J Leukoc Biol* 64(2): 135-46.

Horiuchi, S., Y. Sakamoto, et al. (2003). "Scavenger receptors for oxidized and glycated proteins." *Amino Acids* 25(3-4): 283-92.

Huang, X., C. Gottstein, et al. (1998). "Expression of soluble VEGF receptor 2 and characterization of its binding by surface plasmon resonance." *Biochem Biophys Res Commun* 252(3): 643-8.

Hussain, M. M., D. K. Strickland, et al. (1999). "The mammalian low-density lipoprotein receptor family." *Annu Rev Nutr* 19: 141-72.

Idriss, H. T. and J. H. Naismith (2000). "TNF alpha and the TNF receptor superfamily: structure-function relationship(s)." *Microsc Res Tech* 50(3): 184-95.

Ishigaki, T., I. Ohki, et al. (2005). "Purification, crystallization and preliminary X-ray analysis of the ligand-binding domain of human lectin-like oxidized low-density lipoprotein receptor 1 (LOX-1)." *Acta Crystallograph Sect F Struct Biol Cryst Commun* 61(Pt 5): 524-7.

Johs, A., M. Hammel, et al. (2006). "Modular structure of solubilized human apolipoprotein B-100. Low resolution model revealed by small angle neutron scattering." *J Biol Chem* 281(28): 19732-9.

Kataoka, H., N. Kume, et al. (2000). "Biosynthesis and post-translational processing of lectin-like oxidized low density lipoprotein receptor-1 (LOX-1). N-linked glycosylation affects cell-surface expression and ligand binding." *J Biol Chem* 275(9): 6573-9.

Kawar, Z. S., S. M. Haslam, et al. (2005). "Novel poly-GalNAcbeta 1-4GlcNAc (LacdiNAc) and fucosylated poly-LacdiNAc N-glycans from mammalian cells expressing beta 1,4-N-acetylgalactosaminyltransferase and alpha-1,3-fucosyltransferase." *J Biol Chem* 280(13): 12810-9.

Kita, T., N. Kume, et al. (2001). "Role of oxidized LDL in atherosclerosis." *Ann N Y Acad Sci* 947: 199-205; discussion 205-6.

Kong, W.-J., J. Liu, et al. (2006). "Human low-density lipoprotein receptor gene and its regulation." *J. Molec. Med.* 84(1): 29-36.

Mahley, R. W. (1988). "Apolipoprotein E: cholesterol transport protein with expanding role in cell biology." *Science* 240(4852): 622-30.

McCormack, P. L. and K. Wellington (2004). "Etanercept: in ankylosing spondylitis." *BioDrugs* 18(3): 199-205; discussion 206.

Murase, T., N. Kume, et al. (2000). "Identification of soluble forms of lectin-like oxidized LDL receptor-1." *Arterioscler Thromb Vasc Biol* 20(3): 715-20.

Murray, C. J. and A. D. Lopez (1997). "Global mortality, disability, and the contribution of risk factors: Global Burden of Disease Study." *Lancet* 349(9063): 1436-42.

Nakajima, K., T. Nakano, et al. (2006). "The oxidative modification hypothesis of atherosclerosis: the comparison of atherogenic effects on oxidized LDL and remnant lipoproteins in plasma." *Clin Chim Acta* 367(1-2): 36-47.

Olofsson, S. O. and J. Boren (2005). "Apolipoprotein B: a clinically important apolipoprotein which assembles atherogenic lipoproteins and promotes the development of atherosclerosis." *J Intern Med* 258(5): 395-410.

Park, E. I., Y. Mi, et al. (2005). "The asialoglycoprotein receptor clears glycoconjugates terminating with sialic acid alpha 2,6GalNAc." *Proc Natl Acad Sci USA* 102(47): 17125-9.

Rensen, P. C., L. A. Sliedregt, et al. (2006). "Stimulation of liver-directed cholesterol flux in mice by novel N-acetylgalactosamine-terminated glycolipids with high affinity for the asialoglycoprotein receptor." *Arterioscler Thromb Vasc Biol* 26(1): 169-75.

Rensen, P. C., S. H. van Leeuwen, et al. (2004). "Design and synthesis of novel N-acetylgalactosamine-terminated glycolipids for targeting of lipoproteins to the hepatic asialoglycoprotein receptor." *J Med Chem* 47(23): 5798-808.

Rice, K. G., V. H. Thomas, et al. (2003). "Probing the binding specificity of C-type lectins in vivo." *Methods Enzymol* 363: 90-104.

Robbesyn, F., R. Salvayre, et al. (2004). "Dual role of oxidized LDL on the NF-kappaB signaling pathway." *Free Radic Res* 38(6): 541-51.

Sawamura, T., N. Kume, et al. (1997). "An endothelial receptor for oxidized low-density lipoprotein." *Nature* 386(6620): 73-7.

Schwartzman, S., R. Fleischmann, et al. (2004). "Do anti-TNF agents have equal efficacy in patients with rheumatoid arthritis?" *Arthritis Res Ther* 6 Suppl 2: S3-S11.

Segrest, J. P., M. K. Jones, et al. (2001). "Structure of apolipoprotein B-100 in low density lipoproteins." *J Lipid Res* 42(9): 1346-67.

Selmaj, K. W. (2000). "Tumour necrosis factor and anti-tumour necrosis factor approach to inflammatory demyelinating diseases of the central nervous system." *Ann Rheum Dis* 59 Suppl 1: i94-102.

Shi, X., S. Niimi, et al. (2001). "Characterization of residues and sequences of the carbohydrate recognition domain required for cell surface localization and ligand binding of human lectin-like oxidized LDL receptor." *J Cell Sci* 114 (Pt 7): 1273-82.

Simmons, T., Y. M. Newhouse, et al. (1997). "Human low density lipoprotein receptor fragment. Successful refolding of a functionally active ligand-binding domain produced in *Escherichia coli.*" *J Biol Chem* 272(41): 25531-6.

Smirnova, I. V., T. Sawamura, et al. (2004). "Upregulation of lectin-like oxidized low-density lipoprotein receptor-1 (LOX-1) in endothelial cells by nitric oxide deficiency." *Am J Physiol Renal Physiol* 287(1): F25-32.

Spady, D. K. (1992). "Hepatic clearance of plasma low density lipoproteins." *Semin Liver Dis* 12(4): 373-85.

Tulenko, T. N. and A. E. Sumner (2002). "The physiology of lipoproteins." *J Nucl Cardiol* 9(6): 638-49.

Twisk, J., D. L. Gillian-Daniel, et al. (2000). "The role of the LDL receptor in apolipoprotein B secretion." *J Clin Invest* 105(4): 521-32.

Westerlind, U., J. Westman, et al. (2004). "Ligands of the asialoglycoprotein receptor for targeted gene delivery, part 1: Synthesis of and binding studies with biotinylated cluster glycosides containing N-acetylgalactosamine." *Glycoconj J* 21(5): 227-41.

Xie, Q., S. Matsunaga, et al. (2004). "Human lectin-like oxidized low-density lipoprotein receptor-1 functions as a dimer in living cells." *DNA Cell Biol* 23(2): 111-7.

Zhang, H., X. J. Li, et al. (2003). "Identification and quantification of N-linked glycoproteins using hydrazide chemistry, stable isotope labeling and mass spectrometry." *Nat Biotechnol* 21(6): 660-6.

---

The invention claimed is:

1. A glycan-modified soluble low-density lipoprotein (LDL) receptor, modified to carry a terminal galactose (Gal), N-acetylglucosamine (GlcNAc) or N-acetylgalactosamine (GalNAc), wherein the glycan-modified soluble LDL receptor exhibits an increased circulatory clearance rate relative to an unmodified soluble LDL receptor.

2. The glycan-modified soluble LDL receptor of claim 1, wherein the soluble LDL receptor is a soluble LDL receptor fragment.

3. The glycan-modified soluble LDL receptor according to claim 1, selected from the group consisting of N-acetyl galactosaminated soluble LDLR (sLDLR-Gn), N-acetyl galactosaminated soluble LDLR 25-352 (sLDLR-Gn 25-352), N-acetyl galactosaminated soluble LDLR 25-313 (sLDLR-Gn 25-313), N-acetyl galactosaminated soluble LDLR 1-315 (sLDLR-Gn 1-315) and N-acetyl galactosaminated soluble LDLR Gn-Asn 272 (sLDLR-Gn-Asn-272).

4. A pharmaceutical composition comprising the glycan-modified soluble LDL receptor of claim 1 and a pharmaceutically acceptable carrier.

5. A pharmaceutical composition comprising a pharmaceutically acceptable carrier and the glycan-modified soluble LDL receptor of claim 2 or claim 3.

6. A method for facilitating the clearance of a circulating lipoprotein comprising administering to a subject in need thereof a therapeutically effective amount of the glycan-modified soluble LDL receptor according to claim 1.

7. A method for treating a disease, disorder, or condition whose pathogenesis or course is associated with the levels and/or activity of a lipoprotein, comprising administering to a subject in need thereof a therapeutically effective amount of the glycan-modified soluble LDL receptor according to claim 1.

8. A method for treating hypercholesterolemia comprising administering to a subject in need thereof a therapeutically effective amount of the glycan-modified soluble LDL receptor (sLDLR) according to claim 1.

9. The method according to claim 7, wherein the pathogenesis or course of the disease, disorder, or condition is associated with excess of a lipoprotein in the circulation.

10. The method according to claim 7, wherein the disorder is hypercholesterolemia.

11. The method according to claim 8, for treating familial hypercholesterolemia.

12. The method according to claim 8, wherein the soluble LDL receptor is sLDLR-Gn.

* * * * *

SEQUENCE LISTING

```
<160> NUMBER OF SEQ ID NOS: 24

<210> SEQ ID NO 1
<211> LENGTH: 31
<212> TYPE: DNA
<213> ORGANISM: Artificial Sequence
<220> FEATURE:
<223> OTHER INFORMATION: Synthetic primer

<400> SEQUENCE: 1
cccaagcttc caccatgggg ccctggggct g                                    31

<210> SEQ ID NO 2
<211> LENGTH: 34
<212> TYPE: DNA
<213> ORGANISM: Artificial Sequence
<220> FEATURE:
<223> OTHER INFORMATION: Synthetic primer

<400> SEQUENCE: 2
ccgggatcct tactagcatc ttcgctgggc cacc                                 34

<210> SEQ ID NO 3
<211> LENGTH: 19
<212> TYPE: PRT
<213> ORGANISM: Artificial Sequence
<220> FEATURE:
<223> OTHER INFORMATION: Synthetic peptide

<400> SEQUENCE: 3

Asp Met Ser Asp Glu Val Gly Cys Val Asn Val Thr Leu Cys Glu Gly
1               5                   10                  15

Pro Asn Lys

<210> SEQ ID NO 4
<211> LENGTH: 17
<212> TYPE: PRT
<213> ORGANISM: Artificial Sequence
<220> FEATURE:
<223> OTHER INFORMATION: Synthetic peptide

<400> SEQUENCE: 4

Cys Glu Arg Asn Glu Phe Gln Cys Gln Asp Gly Lys Cys Ile Ser Tyr
```

Lys

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Asn Glu Phe Gln Cys Gln Asp Gly Lys
1               5

<210> SEQ ID NO 6
<211> LENGTH: 14
<212> TYPE: PRT
<213> ORGANISM: Artificial Sequence
<220> FEATURE:
<223> OTHER INFORMATION: Synthetic peptide

<400> SEQUENCE: 6

Asn Glu Phe Gln Cys Gln Asp Gly Lys Cys Ile Ser Tyr Lys
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Cys Ile Ser Tyr Lys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Ser Gly Asp Phe Ser Cys Gly Gly Arg
1               5

<210> SEQ ID NO 9
<211> LENGTH: 12
<212> TYPE: PRT
<213> ORGANISM: Artificial Sequence
<220> FEATURE:
<223> OTHER INFORMATION: Synthetic peptide

<400> SEQUENCE: 9

Ser Gly Asp Phe Ser Cys Gly Gly Arg Val Asn Arg
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

```
Cys Ile Pro Gln Phe Trp Arg
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide

<400> SEQUENCE: 11

Val Asn Arg Cys Ile Pro Gln Phe Trp Arg
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Thr Cys Ser Gln Asp Glu Phe Arg
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

Cys His Asp Gly Lys
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Cys His Asp Gly Lys Cys Ile Ser Arg
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide

<400> SEQUENCE: 15

Gln Phe Val Cys Asp Ser Asp Arg
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Cys Asp Gly Gly Pro Asp Cys Lys
```

<210> SEQ ID NO 17
<211> LENGTH: 14
<212> TYPE: PRT
<213> ORGANISM: Artificial Sequence
<220> FEATURE:
<223> OTHER INFORMATION: Synthetic peptide

<400> SEQUENCE: 17

Asp Lys Ser Asp Glu Glu Asn Cys Ala Val Ala Thr Cys Arg
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

Gln Cys Asp Arg Glu Tyr Asp Cys Lys
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide

<400> SEQUENCE: 19

Glu Tyr Asp Cys Lys
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide

<400> SEQUENCE: 20

Cys His Ser Gly Glu Cys Ile Thr Leu Asp Lys
1               5                   10

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Val Cys Asn Met Ala Arg
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

Val Cys Asn Met Ala Arg Asp Cys Arg
1               5

```
<210> SEQ ID NO 23
<211> LENGTH: 8
<212> TYPE: PRT
<213> ORGANISM: Artificial Sequence
<220> FEATURE:
<223> OTHER INFORMATION: Synthetic peptide

<400> SEQUENCE: 23

Asp Trp Ser Asp Glu Pro Ile Lys
1               5

<210> SEQ ID NO 24
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 24

Cys Asp Xaa Xaa Xaa Asp Cys Xaa Asp Xaa Ser Asp Glu
1               5                   10
```